(12) United States Patent
Hilpert et al.

(10) Patent No.: US 8,314,253 B2
(45) Date of Patent: Nov. 20, 2012

(54) BRIDGED TETRAHYDRONAPHTHALENE DERIVATIVES

(75) Inventors: Kurt Hilpert, Allschwil (CH); Francis Hubler, Allschwil (CH); Dorte Renneberg, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 25 days.

(21) Appl. No.: 13/125,424

(22) PCT Filed: Oct. 21, 2009

(86) PCT No.: PCT/IB2009/054634
§ 371 (c)(1),
(2), (4) Date: Apr. 21, 2011

(87) PCT Pub. No.: WO2010/046855
PCT Pub. Date: Apr. 29, 2010

(65) Prior Publication Data
US 2011/0263648 A1    Oct. 27, 2011

(30) Foreign Application Priority Data

Oct. 22, 2008    (WO) .................. PCT/IB2008/054354

(51) Int. Cl.
*A61K 31/454* (2006.01)
*A61K 31/4184* (2006.01)
*C07D 401/04* (2006.01)
*C07D 235/14* (2006.01)

(52) U.S. Cl. ..................... 548/309.7; 546/199; 514/322; 514/394

(58) Field of Classification Search ................ 548/309.7
See application file for complete search history.

(56) References Cited

U.S. PATENT DOCUMENTS

| 4,808,605 A | 2/1989 | Branca et al. |
| 8,202,885 B2 | 6/2012 | Hilpert et al. |
| 2011/0039905 A1 | 2/2011 | Hubler et al. |
| 2011/0207815 A1 | 8/2011 | Hilpert et al. |

FOREIGN PATENT DOCUMENTS

| EP | 0 268 148 | 11/1987 |
| WO | WO 2008/132679 | 11/2008 |

OTHER PUBLICATIONS

PCT/IB2009/054634 Written Opinion, Jan. 4, 2010, Actelion Pharmaceuticals Ltd.
Clozel, J-P., et al., "Voltage-Gated T-Type $Ca^{2+}$ Channels and Heart Failure", Proceedings of the Association of American Physicians, vol. 111, pp. 429-437, (1999).
Crooks, P.A., et al., "Synthesis of *endo*-12-aminotricyclo[6.3.2.0]trideca-2(7).3.5-triene-12-*exo*-carboxylic acid: A novel, conformationally restricted phenylalanine analogue", Synth. Comm., vol. 24, pp. 3813-3819, (2002).
Döring, H.J., "The Isolated Perfused Heart According to Langendorff Technique—Function—Application", Physiologie Bohemoslovaca, vol. 39(6), pp. 481-504, (1990).
du Souich, P., et al., "Nonlinear Kinetics and Pharmacologic Response to Mibefradil", Clinical Pharmacol Ther, vol. 67, pp. 249-257, (2000).
Essers, M., et al., "Chemical consequences of fluorine substitution, Part 4, Diels-Alder reactions of fluorinated *p*-benzoquinones with Dane's diene, Synthesis of fluorinated D-homosteroids", J. Chem. Soc., Perkin Trans., vol. 23. pp. 2719-2728, (2002).
Fischer, A., et al., "*ipso* Nitration, XXIX, Nitration of substituted 4-methylanisoles and phenols", Can. J. Chem., vol. 65, pp. 1233-1240, (1987).
Gould, P.L., "Salt Selection for Basic Drugs", International Journal of Pharmaceutics, vol. 33, pp. 201-217, (1986).
Greene, T.W., et al., Protective Groups in Organic Synthesis, 2nd Edition, Wiley New York, (1991), Table of Contents Only.
Hammershøj, P., et al., "Synthesis and Properties of 2.3-Dialkynyl-1.4-benzoquinones", Eur. J. Org. Chem., pp. 2786-2794, (2006).
Honda, M., et al., "Divergent Renal Vasodilator Action of L- and T-type Calcium Antagonists in vivo", Journal of Hypertension, vol. 19, pp. 2031-2037, (2001).
Kligfield. P., et al., "A Model of Graded Ischemia in the Isolated Perfused Rat Heart", Journal of Applied Physiology, vol. 40, No. 6, pp. 1004-1008, (1976).
Ramires, F.J.A., et al., "Myocardial Fibrosis Associated with Aldosterone or Angiotensin II Administration: Attenuation by Calcium Channel Blockade", J. Mol. Cell. Cardiol., vol. 30, pp. 475-483, (1998).
Remington, The Science and Practice of Pharmacy, 21$^{st}$ Edition (2005), Part 5, "Pharmaceutical Manufacturing" [published by Lippincott Williams & Wilkins], Table of Contents Only.
Villame, J., et al. "Effects of Mibefradil, a T- and L-Type Calcium Channel Blocker, on Cardiac Remodeling in the UM-X7.1 Cardiomyopathic Hamster", Cardiovascular Drugs and Therapy, vol. 15, pp. 41-28, (2001).
Wandel, C., et al., "Miberfradil is a P-Glycoprotein Substrate and a Potent Inhibitor of Both P-Glycoprotein and CYP3A in Vitro", Drug Metabolism and Disposition, vol. 28, No. 8, pp. 895-898, (2000).

*Primary Examiner* — Laura L. Stockton
(74) *Attorney, Agent, or Firm* — Hoxie & Associates LLC

(57) ABSTRACT

The invention relates to compounds of formula (I) wherein $R^1, R^2, R^3, R^4$, A, B, W and n are as defined in the description, and to pharmaceutically acceptable salts of such compounds. These compounds are useful as calcium channel blockers.

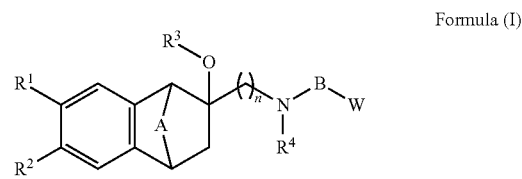

Formula (I)

14 Claims, No Drawings

BRIDGED TETRAHYDRONAPHTHALENE DERIVATIVES

CROSS REFERENCE TO RELATED APPLICATIONS

This application is a US filing under 35 USC 371 of PCT/IB2009/054634 filed on Oct. 21, 2009, which claims the benefit of Application No. PCT/IB2008/054354 filed on Oct. 22, 2008.

FIELD OF THE INVENTION

The present invention relates to novel bridged tetrahydronaphthalene derivatives and their use as potent calcium channel blockers in the treatment or prevention of angina pectoris, ischemia, arrhythmias, high blood pressure and cardiac insufficiency, to pharmaceutical compositions containing these derivatives and to processes for their preparation. In particular, such derivatives may be used alone or in pharmaceutical compositions for the treatment of both chronic and acute of angina pectoris, cardiac arrhythmias, high blood pressure, cardiac insufficiency, renal disease, diabetes and its complications, hyperaldosteronism, epilepsy, neuropathic pain, Parkinson's disease, depression anxiety, sleep disturbances, psychosis, schizophrenia, contraception and cancer in humans and other mammals.

BACKGROUND OF THE INVENTION

Many cardiovascular disorders have been associated with a 'calcium overload' resulting from an abnormal elevated calcium influx through the plasma membrane of cardiac and vascular smooth muscle cells. There are 3 major pathways through which extracellular calcium can enter these cells: 1) receptor-activated calcium channels, 2) ligand-gated calcium channels and 3) voltage-operated calcium channels (VOCs).

VOCs have been classified into 6 main categories: L (Long-lasting), T (Transient), N (Neuronal), P (Purkinje cells), Q (after P) and R (Remaining or Resistant).

L-type calcium channels are responsible for the inward movement of calcium that initiates contraction in cardiac and smooth muscle cells suggesting a putative application for blockers of these channels in the cardiovascular field. In this view, L-type calcium channel blockers have been used in clinic since the early 60 s and are now recommended as a first line of treatment for systolic-diastolic hypertension and angina pectoris.

T-type calcium channels are found in various tissues such as coronary and peripheral vasculature, SA node and Purkinje fibres, brain, adrenal glands and in the kidney. This broad distribution suggests a T-type channel blocker to have a putative cardiovascular protection, to have en effect on sleep disorders, mood disorders, depression, migraine, hyperaldosteroneemia, preterm labor, urinary incontinence, brain aging or neurodegenerative disorders such as Alzheimers disease.

Mibefradil (Posicor®), the first L-type and T-type calcium channels blocker demonstrated a superior effect over calcium channel blockers, which target the L channel predominantly.

Mibefradil was used for the treatment of hypertension and angina without showing negative side-effects often seen by L channel blockers like inotropy, reflex tachycardia, vasoconstrictive hormone release or peripheral edema. Additionally mibefradil showed a potentially cardioprotective effect (Villame, Cardiovascular Drugs and Therapy 15, 41-28, 2001; Ramires, J Mol Cell Cardiol 30, 475-83, 1998), a renal protective effect (Honda, Hypertension 19, 2031-37, 2001), and showed a positive effect in the treatment of heart failure (Clozel, Proceedings Association American Physicians 111, 429-37, 1999)

Despite the enormous demand for a compound of this profile, mibefradil was withdrawn from the market in 1998 (one year after its launch), due to unacceptable CYP 3A4 drug interactions. Moreover, ECG abnormalities (i.e. QT prolongations) and interaction with the MDR-1 mediated digoxin efflux were also reported. (du Souich, Clin Pharmacol Ther 67, 249-57, 2000; Wandel, Drug Metab Dispos 28, 895-8, 2000).

There clearly is a demand for novel compounds, which act as T-type calcium channel blockers but have an improved safety profile with respect to mibefradil.

DESCRIPTION OF THE INVENTION

The compounds of the present invention are potent T/L channel blockers and therefore useful in diseases where both, T and L channels are involved.

1) A first aspect of the invention relates to compounds of the formula (I)

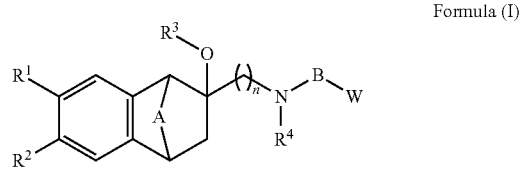

Formula (I)

wherein $R^1$ and $R^2$ independently represent hydrogen or halogen;

A represents a linear $(C_{1-3})$alkan-diyl chain, wherein said linear $(C_{1-3})$alkan-diyl chain is optionally substituted with one or more methyl;

$R^3$ represents hydrogen, $(C_{1-5})$alkyl, or —CO—$R^{31}$;

$R^{31}$ represents $(C_{1-5})$alkyl, $(C_{1-3})$fluoroalkyl, $(C_{3-6})$cycloalkyl, $(C_{3-6})$cycloalkyl-$(C_{1-3})$alkyl, $(C_{1-5})$alkoxy, $(C_{1-2})$alkoxy-$(C_{1-3})$alkyl, or $R^{32}R^{33}N$—;

$R^{32}$ represents $(C_{1-5})$alkyl;

$R^{33}$ represents hydrogen, or $(C_{1-5})$alkyl;

n represents the integer 1, 2, 3, or 4;

B represents a group —$(CH_2)_m$—, wherein m represents the integer 1, 2, 3, 4, or 5; or B together with $R^4$ and the nitrogen atom to which B and $R^4$ are attached forms a 4- to 6-membered saturated ring, wherein said ring may optionally be mono-substituted with phenyl;

$R^4$ represents hydrogen; $(C_{1-5})$alkyl; $(C_{1-2})$alkoxy-$(C_{1-3})$alkyl; $(C_{1-3})$fluoroalkyl; $(C_{3-6})$cycloalkyl; $(C_{3-6})$cycloalkyl-$(C_{1-3})$alkyl; or $R^4$ together with B and the nitrogen atom to which $R^4$ and B are attached forms a 4- to 6-membered saturated ring, wherein said ring may optionally be mono-substituted with phenyl; and W represents

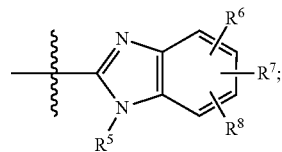

wherein

R$^5$ represents hydrogen, or (C$_{1-5}$)alkyl; and

R$^6$, R$^7$ and R$^8$ independently represent hydrogen, halogen, (C$_{1-5}$)alkyl, hydroxy, (C$_{1-5}$)alkoxy, —O—CO—(C$_{1-5}$)alkyl, (C$_{1-3}$)fluoroalkyl, (C$_{1-3}$)fluoroalkoxy, —COOH, —CO—(C$_{1-5}$)alkoxy, (C$_{1-2}$)alkoxy-(C$_{1-4}$)alkoxy, or —NH—CO—(C$_{1-5}$)alkyl.

The following paragraphs provide definitions of the various chemical moieties for the compounds according to the invention and are intended to apply uniformly throughout the specification and claims, unless an otherwise expressly set out definition provides a broader or narrower definition.

In this patent application, a bond interrupted by a wavy line shows the point of attachment of the radical drawn. For example, the radical drawn below

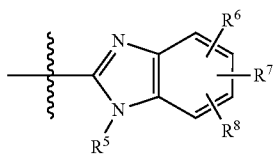

is a benzimidazol-2-yl group which is further substituted with R$^5$, R$^6$, R$^7$ and R$^8$.

The term "(C$_{1-5}$)alkyl" means a straight-chain or branched-chain alkyl group with 1 to 5 carbon atoms. Preferred are groups with 1 to 4 carbon atoms. The term "(C$_{x-y}$)alkyl" (x and y being an integer) refers to a straight or branched chain alkyl group containing x to y carbon atoms. Examples of (C$_{1-5}$)alkyl groups are methyl, ethyl, n-propyl, isopropyl, n-butyl, sec.-butyl, tert.-butyl, isobutyl, n-pentyl, and isopentyl. Preferred are methyl, ethyl, n-propyl, and isopropyl. Most preferred is methyl. For the substituent R$^4$, and R$^5$ a preferred example of a (C$_{1-5}$)alkyl group is methyl. For the substituent R$^{31}$ a preferred example of a (C$_{1-5}$)alkyl group is isopropyl.

The term "linear (C$_{1-3}$)alkan-diyl chain, wherein said linear (C$_{1-3}$)alkan-diyl chain is optionally substituted with one or more methyl" as used for the substituent A means a straight-chain alkan-diyl group with 1 to 3 carbon atoms which is unsubstituted, or wherein 1 up to the maximum of hydrogen atoms have been replaced by methyl. Examples of such groups are methylen, ethane-1,1-diyl, propane-2,2-diyl, ethane-1,2-diyl, 1,2-dimethyl-ethane-1,2-diyl, 1,1-dimethyl-ethane-1,2-diyl, 2,2-dimethyl-ethane-1,2-diyl, 1,1,2,2-tetramethyl-ethane-1,2-diyl, propane-1,3-diyl, and 2,2-dimethyl-propane-1,3-diyl. Preferred are methylen, propane-2,2-diyl, ethane-1,2-diyl, and propane-1,3-diyl. Most preferred are ethane-1,2-diyl, and propane-1,3-diyl.

The term "(C$_{1-3}$)fluoroalkyl" means a straight-chain or branched-chain (C$_{1-3}$)alkyl group which is substituted with 1 to 7 fluorine atoms. Examples of (C$_{1-3}$)fluoroalkyl groups are trifluoromethyl, 2-fluoroethyl, 2,2-difluoroethyl, 2,2,2-trifluoroethyl, and pentafluoroethyl. Preferred are trifluoromethyl, 2,2,2-trifluoroethyl, and pentafluoroethyl. Most preferred are (especially) trifluoromethyl and 2,2,2-trifluoroethyl. For the substituent R$^{31}$, 2,2,2-trifluoroethyl is preferred. For the substituent R$^4$, 2-fluoroethyl, 2,2-difluoroethyl and 2,2,2-trifluoroethyl are preferred.

The term "(C$_{1-3}$)fluoroalkoxy" means a straight-chain or branched-chain (C$_{1-3}$)alkyl-O— group which is substituted with 1 to 7 fluorine atoms. Examples of (C$_{1-3}$)fluoroalkoxy groups are trifluoromethoxy, and 2,2,2-trifluoroethoxy. Preferred is trifluoromethoxy.

The term "(C$_{3-6}$)cycloalkyl" means a saturated cyclic alkyl group with 3 to 6 carbon atoms. Examples of (C$_{3-6}$)cycloalkyl groups are cyclopropyl, cyclobutyl, cyclopentyl and cyclohexyl. Preferred is cyclopropyl.

The term "(C$_{3-6}$)cycloalkyl-(C$_{1-3}$)alkyl" means a (C$_{3-6}$)cycloalkyl group as defined before which is attached to the rest of the molecule via a (C$_{1-3}$)alkyl group as defined before. Examples are cyclopropyl-methyl, cyclopentyl-methyl and cyclohexyl-methyl; preferred is cyclopropyl-methyl.

Examples of groups wherein "B together with R$^4$ and the nitrogen atom to which B and R$^4$ are attached forms a 4- to 6-membered saturated ring, wherein said ring may optionally be mono-substituted with phenyl" are azetidin-3-yl, pyrrolidin-3-yl, piperidin-3-yl, piperidin-4-yl and 4-phenyl-piperidin-4-yl. Preferred are piperidin-3-yl, piperidin-4-yl and 4-phenyl-piperidin-4-yl. In another embodiment preferred are those examples wherein the thus formed 4- to 6-membered saturated ring is unsubstituted, such as azetidin-3-yl, pyrrolidin-3-yl, piperidin-3-yl and piperidin-4-yl, especially piperidin-3-yl and piperidin-4-yl.

The term "(C$_{1-5}$)alkoxy" means a group of the formula (C$_{1-5}$)alkyl-O— in which the term (C$_{1-5}$)alkyl has the previously given significance. The term "(C$_{x-y}$)alkoxy" (x and y being an integer) refers to a straight or branched chain alkoxy group containing x to y carbon atoms. Examples of (C$_{1-5}$)alkoxy groups are methoxy, ethoxy, n-propoxy, isopropoxy, n-butoxy, isobutoxy, sec-butoxy and tert.-butoxy. Preferred are methoxy and ethoxy.

The term "(C$_{1-2}$)alkoxy-(C$_{1-3}$)alkyl" means a (C$_{1-2}$)alkoxy-group as defined before which is attached to the rest of the molecule via a (C$_{1-3}$)alkyl group as defined before. Examples are methoxy-methyl, 2-methoxy-ethyl, 2-methoxy-2-methyl-ethyl and 3-methoxy-propyl. For the substituent R$^{31}$, 2-methoxy-2-methyl-ethyl and especially methoxy-methyl are preferred.

An example of a "(C$_{1-2}$)alkoxy-(C$_{1-4}$)alkoxy" group is 2-methoxy-ethoxy.

An example of a "—O—CO—(C$_{1-6}$)alkyl" group is —O—CO—CH(CH$_3$)$_2$.

An example of a "—CO—(C$_{1-6}$)alkoxy" group is —CO—OCH$_3$.

An example of a "—NH—CO—(C$_{1-6}$)alkyl" group is acetamido.

The term "halogen" means fluorine, chlorine, bromine or iodine, especially fluorine or chlorine.

2) A further embodiment of the invention relates to compounds of formula (I) according to embodiment 1), wherein the configuration of the bridged tetrahydronaphthalene moiety is such that the R$^3$—O— substituent and the bridge A of the tetrahydronaphthalene moiety are in cis relation (i.e. the absolute configuration is as depicted in either formula (I$_{E1}$) or formula (I$_{E2}$) below).

3) A further embodiment of the invention relates to compounds of formula (I) according to embodiments 1) or 2), wherein the absolute configuration is as depicted in formula (I$_{E1}$)

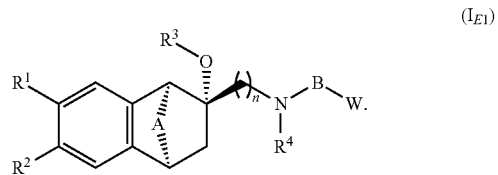

(I$_{E1}$)

4) A further embodiment of the invention relates to compounds of formula (I) according to embodiments 1) or 2), wherein the absolute configuration depicted is as in formula (I$_{E2}$)

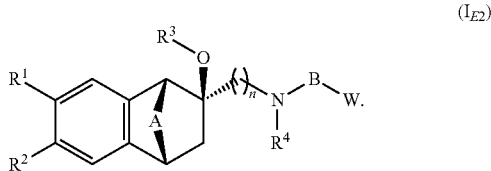

5) A further embodiment of the invention relates to compounds of formula (I) according to any one of embodiments 1) to 4), wherein R$^1$ and R$^2$ both represent hydrogen.

6) A further embodiment of the invention relates to compounds of formula (I) according to any one of embodiments 1) to 4), wherein R$^1$ and R$^2$ both represent halogen (especially fluorine).

7) A further embodiment of the invention relates to compounds of formula (I) according to any one of embodiments 1) to 6), wherein A represents —(CH$_2$)$_p$—, wherein p represents the integer 2 or 3.

8) A further embodiment of the invention relates to compounds of formula (I) according to embodiment 7), wherein p represents the integer 2.

9) A further embodiment of the invention relates to compounds of formula (I) according to embodiment 7), wherein p represents the integer 3.

10) A further embodiment of the invention relates to compounds of formula (I) according to any one of embodiments 1) to 9), wherein R$^3$ represents hydrogen, or —CO—R$^{31}$.

11) A further embodiment of the invention relates to compounds of formula (I) according to any one of embodiments 1) to 10), wherein R$^3$ represents —CO—R$^{31}$.

12) A further embodiment of the invention relates to compounds of formula (I) according to any one of embodiments 1) to 11), wherein R$^{31}$ represents (C$_{1-5}$)alkyl, (C$_{1-3}$)fluoroalkyl, (C$_{3-6}$)cycloalkyl, or (C$_{1-2}$)alkoxy-(C$_{1-3}$)alkyl.

13) A further embodiment of the invention relates to compounds of formula (I) according to any one of embodiments 1) to 12), wherein R$^{31}$ represents (C$_{1-5}$)alkyl, (C$_{1-3}$)fluoroalkyl, or (C$_{3-6}$)cycloalkyl.

14) A further embodiment of the invention relates to compounds of formula (I) according to any one of embodiments 1) to 13), wherein
R$^{31}$ represents (C$_{1-5}$)alkyl (preferred), or (C$_{3-6}$)cycloalkyl.

15) A further embodiment of the invention relates to compounds of formula (I) according to any one of embodiments 1) to 10), wherein R$^3$ represents hydrogen.

16) A further embodiment of the invention relates to compounds of formula (I) according to any one of embodiments 1) to 15), wherein B represents a group —(CH$_2$)$_m$—.

17) A further embodiment of the invention relates to compounds of formula (I) according to any one of embodiments 1) to 15), wherein B together with R$^4$ and the nitrogen atom to which B and R$^4$ are attached forms a 4- to 6-membered saturated ring, wherein said ring may optionally be mono-substituted with phenyl.

18) A further embodiment of the invention relates to compounds of formula (I) according to any one of embodiments 1) to 16), wherein m represents the integer 1 to 3 (preferably 2 or 3).

19) A further embodiment of the invention relates to compounds of formula (I) according to any one of embodiments 1) to 16), wherein m represents the integer 3.

20) A further embodiment of the invention relates to compounds of formula (I) according to any one of embodiments 1) to 19), wherein n represents the integer 2.

21) A further embodiment of the invention relates to compounds of formula (I) according to any one of embodiments 1) to 20), wherein R$^4$ represents (C$_{1-5}$)alkyl.

22) A further embodiment of the invention relates to compounds of formula (I) according to any one of embodiments 1) to 21), wherein
R$^6$, R$^7$ and R$^8$ independently represent hydrogen, halogen, (C$_{1-5}$)alkyl, (C$_{1-5}$)alkoxy, (C$_{1-3}$)fluoroalkyl, or (C$_{1-3}$)fluoroalkoxy (especially hydrogen, (C$_{1-5}$)alkyl, or (C$_{1-5}$)alkoxy).

23) A further embodiment of the invention relates to compounds of formula (I) according to any one of embodiments 1) to 22), wherein W represents

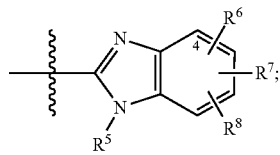

wherein one of R$^6$, R$^7$ or R$^8$ is (C$_{1-5}$)alkoxy in position 4 of the benzimidazole ring.

24) A further embodiment of the invention relates to compounds of formula (I) according to embodiment 23), wherein W represents

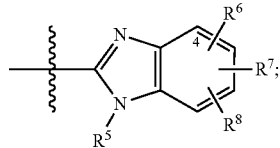

wherein one of R$^6$, R$^7$ or R$^8$ is (C$_{1-5}$)alkoxy (especially methoxy) in position 4 of the benzimidazole ring, one of R$^6$, R$^7$ or R$^8$ is hydrogen, and the remaining is selected from the group consisting of hydrogen, (C$_{1-5}$)alkyl, and (C$_{1-5}$)alkoxy.

25) A further embodiment of the invention relates to compounds of formula (I) according to embodiment 24), wherein W represents

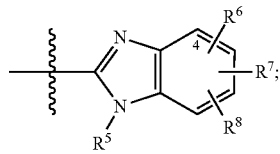

wherein one of R$^6$, R$^7$ or R$^8$ is (C$_{1-5}$)alkoxy (especially methoxy) in position 4 of the benzimidazole ring, one of R$^6$, R$^7$ or R$^8$ is hydrogen and the remaining is selected from (C$_{1-5}$) alkoxy (especially methoxy).

26) A further embodiment of the invention relates to compounds of formula (I) according to any one of embodiments 22) to 25), wherein W represents

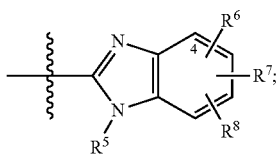

wherein two of $R^6$, $R^7$ or $R^8$ are in position 4 and 7, respectively, of the benzimidazole ring; wherein said two of $R^6$, $R^7$ or $R^8$ are preferably different from hydrogen.

27) A further embodiment of the invention relates to compounds of formula (I) according to any one of embodiments 1) to 26), wherein W represents

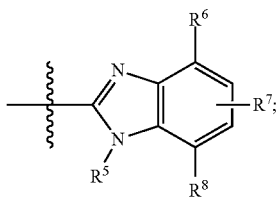

wherein $R^6$ and $R^8$ are independently ($C_{1-5}$)alkoxy (especially methoxy), and $R^7$ represents hydrogen.

28) A further embodiment of the invention relates to compounds of formula (I) according to any one of embodiments 1) to 22), wherein $R^6$, $R^7$ and $R^8$ all represent hydrogen.

29) A further embodiment of the invention relates to compounds of formula (I) according to any one of embodiments 1) to 28), wherein $R^5$ represents hydrogen.

30) A further embodiment of the invention relates to compounds of formula (I) according to any one of embodiments 1) to 28), wherein $R^5$ represents ($C_{1-5}$)alkyl.

31) A further embodiment of the invention relates to compounds of formula (I) according to embodiment 1) which are also compounds of formula ($I_{CE}$)

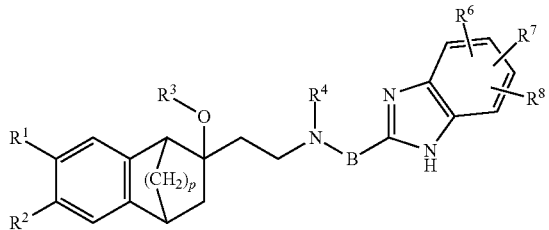

Formula ($I_{CE}$)

wherein $R^1$ and $R^2$ independently represent hydrogen, or halogen (especially fluorine); and preferably $R^1$ and $R^2$ are both the same;

p represents the integer 2 or 3;

$R^3$ represents hydrogen, ($C_{1-6}$)alkoxy (especially methoxy), or —CO—$R^{31}$;

$R^{31}$ represents ($C_{1-6}$)alkyl, ($C_{1-3}$)fluoroalkyl, ($C_{3-6}$)cycloalkyl, or ($C_{1-2}$)alkoxy-($C_{1-3}$)alkyl;

B represents a group —$(CH_2)_m$—, wherein m represents the integer 3; or B together with $R^4$ and the nitrogen atom to which B and $R^4$ are attached forms a 4- to 6-membered (especially 6-membered) saturated ring, wherein said ring may optionally be mono-substituted with phenyl;

$R^4$ represents ($C_{1-5}$)alkyl; or $R^4$ together with B and the nitrogen atom to which $R^4$ and B are attached forms a 4- to 6-membered (especially 6-membered) saturated ring, wherein said ring may optionally be mono-substituted with phenyl;

$R^7$ represents hydrogen; and $R^6$ and $R^8$ independently represent hydrogen, ($C_{1-6}$)alkyl, or ($C_{1-6}$)alkoxy.

The present invention also includes isotopically, especially $^2H$ (deuterium) labelled compounds of formula (I) which compounds are identical to the compound of formula (I) wherein one or more atoms have been replaced by an atom having the same atomic number but an atomic mass different from the atomic mass usually found in nature. Isotopically labelled, especially $^2H$ (deuterium) labelled compounds of formula (I) and salts thereof are within the scope of the present invention. Substitution of hydrogen with the heavier isotope $^2H$ (deuterium) may lead to greater metabolic stability, resulting eg. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or labelled with one or more deuterium atoms. In a sub-embodiment, the compounds of formula (I) are not isotopically labelled. Isotopically labelled compounds of formula (I) may be prepared in analogy to the methods described hereinafter, but using the appropriate isotopic variation of suitable reagents or starting materials.

The compounds of formula (I) contain stereogenic or asymmetric centers, such as asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formulae (I), ($I_{CE}$), ($I_{E1}$), and/or ($I_{E2}$) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* 1986, 33, 201-217.

In one embodiment examples of preferred compounds of formula (I) are selected from the group consisting of:

(1R*,8R*,9R*)-9-(2-{[3-(1H-Benzoimidazol-2-yl)-propyl]-methyl-amino}-ethyl)-tricyclo[6.2.2.0$^{2,7}$]dodeca-2,4,6-trien-9-ol;

Methoxy-acetic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Isobutyric acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Cyclopropanecarboxylic acid (1R*,8R*,9R*)-9-(2-{[3-(1H-benzoimidazol-2-yl)-propyl]methyl-amino}-ethyl)-tricyclo[6.2.2.0$^{2,7}$]dodeca-2,4, 6-trien-9-yl ester;

(1S,8S,9S)-9-(2-{[3-(1H-Benzoimidazol-2-yl)-propyl]-methyl-amino}-ethyl)-tricyclo[6.2.2.0$^{2,7}$]dodeca-2,4,6-trien-9-ol;

(1R,8R,9R)-9-(2-{[3-(1H-Benzoimidazol-2-yl)-propyl]-methyl-amino}-ethyl)-tricyclo[6.2.2.0$^{2,7}$]dodeca-2,4,6-trien-9-ol;

Isobutyric acid (1S,8S,9S)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Isobutyric acid (1R,8R,9R)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

(1R*,8R*,9R*)-[3-(1H-Benzoimidazol-2-yl)-propyl]-[2-(9-methoxy-tricyclo[6.2.2.0$^{2,7}$]dodeca-2,4,6-trien-9-yl)-ethyl]-methyl-amine;

(1R*,8R*,9S*)-9-(2-{[3-(1H-Benzoimidazol-2-yl)-propyl]-methyl-amino}ethyl)-tricyclo[6.2.2.0$^{2,7}$]dodeca-2,4,6-trien-9-ol;

Isobutyric acid (1R*,8R*,9S*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

(1R*,8R*,9R*)-9-{2-[4-(1H-Benzoimidazol-2-yl)-piperidin-1-yl]-ethyl}-tricyclo[6.2.2.0$^{2,7}$]dodeca-2,4,6-trien-9-ol;

Isobutyric acid (1R*,8R*,9R*)-9-{2-[4-(1H-benzoimidazol-2-yl)-piperidin-1-yl]-ethyl}-tricyclo[6.2.2.0$^{2,7}$]dodeca-2,4,6-trien-9-yl ester;

(1R*,8R*,9R*)-9-{2-[(3RS)-3-(1H-Benzoimidazol-2-yl)-piperidin-1-yl]-ethyl}-tricyclo[6.2.2.0$^{2,7}$]dodeca-2,4,6-trien-9-ol;

Isobutyric acid (1R*,8R*,9R*)-9-{2-[(3RS)-3-(1H-benzoimidazol-2-yl)-piperidin-1-yl]-ethyl}-tricyclo[6.2.2.0$^{2,7}$]dodeca-2,4,6-trien-9-yl ester;

(1R*,8R*,9R*)-9-{2-[4-(1H-Benzoimidazol-2-yl)-4-phenyl-piperidin-1-yl]-ethyl}-tricyclo[6.2.2.0$^{2,7}$]dodeca-2,4,6-trien-9-ol;

Isobutyric acid (1R*,8R*,9R*)-9-{2-[4-(1H-benzoimidazol-2-yl)-4-phenyl-piperidin-1-yl]-ethyl}-tricyclo[6.2.2.0$^{2,7}$]dodeca-2,4,6-trien-9-yl ester;

(1R*,8R*,9R*)-9-(2-{[3-(1H-Benzoimidazol-2-yl)-propyl]-methyl-amino}-ethyl)-4,5-difluoro-tricyclo[6.2.2.0$^{2,7}$]dodeca-2,4,6-trien-9-ol;

Isobutyric acid (1R*,8R*,9R*)-9-(2-{[3-(1H-benzoimidazol-2-yl)-propyl]-methyl-amino}-ethyl)-4,5-difluoro-tricyclo[6.2.2.0$^{2,7}$]dodeca-2,4,6-trien-9-yl ester;

(1R*,8R*,12R*)-12-(2-{[3-(1H-Benzoimidazol-2-yl)-propyl]-methyl-amino}-ethyl)-tricyclo[6.3.2.0$^{2,7}$]trideca-2,4,6-trien-12-ol;

Methoxy-acetic acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;

Isobutyric acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;

(1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-ol;

(1R,8R,12R)-12-(2-{[3-(1H-Benzoimidazol-2-yl)-propyl]-methyl-amino}-ethyl)-tricyclo[6.3.2.0$^{2,7}$]trideca-2,4,6-trien-12-ol;

Isobutyric acid (1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-yl ester;

Isobutyric acid (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;

(1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol;

(1R,8R,12R)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol;

Isobutyric acid (1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-yl ester;

Isobutyric acid (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester;

3,3,3-Trifluoro-propionic acid (1S,8S,12S)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester;

3,3,3-Trifluoro-propionic acid (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester;

(1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol;

(1R,8R,12R)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol;

Isobutyric acid (1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-yl ester;

Isobutyric acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;

3,3,3-Trifluoro-propionic acid (1S,8S,12S)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;

3,3,3-Trifluoro-propionic acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;

(1R*,8R*,12R*)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol;

Isobutyric acid (1R*,8R*,12R*)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester;

(1S,8S,12S)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol;

(1R,8R,12R)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol;

Isobutyric acid (1S,8S,12S)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester; and Isobutyric acid (1R,8R,12R)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester.

The relative configuration of stereoisomers is denoted as follows: for example, (1R*,8R*,9R*)-[3-(1H-Benzoimidazol-2-yl)-propyl]-[2-(9-methoxy-tricyclo[6.2.2.0$^{2,7}$]dodeca-2,4,6-trien-9-yl)-ethyl]-methyl-amine denominates (1R,8R,9R)-[3-(1H-Benzoimidazol-2-yl)-propyl]-[2-(9-methoxy-tricyclo[6.2.2.0$^{2,7}$]dodeca-2,4,6-trien-9-yl)-ethyl]-methyl-amine, or (1S,8S,9S)-[3-(1H-Benzoimidazol-2-yl)-propyl]-[2-(9-methoxy-tricyclo[6.2.2.0$^{2,7}$]dodeca-2,4,6-trien-9-yl)-ethyl]-methyl-amine, or mixtures of these two enantiomers such as for example a racemate.

The compounds of formulae (I), (I$_{CE}$), (I$_{E1}$) and/or (I$_{E2}$) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition 2005, Part 5, "Pharmaceutical Manufacturing" [published by Lippincott Williams & Wilkins]) by bringing the described compounds of formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I), or pharmaceutically acceptable salts thereof, are useful in the preparation of a medicament, and/or are suitable for the treatment or prevention of chronic stable angina, hypertension, ischemia (renal and cardiac), cardiac arrhythmias including atrial fibrillation, cardiac hypertrophy, or congestive heart failure.

The compounds of formula (I), or pharmaceutically acceptable salts thereof, are further also useful in the preparation of a medicament, and/or are suitable, for the following disease groups alone or in any combination:

for the treatment of renal diseases, diabetes and its complications, hyperaldosteronism, epilepsy, neuropathic pain, or cancer in humans and other mammals;

for use as anti-fibrillatory agent, anti-asthmatic agent, anti-atherosclerotic agent, additive to cardioplegic solutions for pulmonary bypasses, adjunct to thrombolytic therapy, as antiaggregant agent, or as agent for the treatment of unstable angina;

for the treatment or prophylaxis of hypertension, especially portal hypertension, hypertension secondary to treatment with erythropoietin and low renin hypertension;

for use in hypoxic or ischemic diseases, or as anti ischemic agent for the treatment of e.g. cardiac, renal and cerebral ischemia and reperfusion (e.g. occurring after cardiopulmonary bypass surgery), coronary and cerebral vasospasm and the like, therapy for peripheral vascular diseases (e.g. Raynaud's disease, intermittent claudication, Takayashus disease), sickle cell disease including initiation and/or evolution of the pain crisis;

for the treatment or prophylaxis of disorders related to renal, glomerular and mesangial cell function, including acute and chronic renal failure, diabetic nephropathy, hypertension-induced nephropathy, glomerular injury, renal damage related to age or dialysis, nephrosclerosis, nephrotoxicity related to imaging and contrast agent and to cyclosporine, renal ischemia, primary vesicoureteral reflux, or glomerulosclerosis;

for use in therapy for myocardial infarction, treatment of cardiac hypertrophy, primary and secondary pulmonary hypertension, therapy for congestive heart failure including inhibition of fibrosis, inhibition of left ventricular dilatation, remodelling and dysfunction, or restenosis following angioplasty or stenting;

for the treatment of endotoxemia or endotoxin shock, or hemorrrhagic shock;

for the treatment of sexual dysfunction in both men (erectile dysfunction e.g. due to diabetes mellitus, spinal cord injury, radical prostatectomy, psychogenic etiology and other causes) and women by improving blood flow to the genitalia, especially corpus cavernosum;

for the prevention and/or reduction of cancer or end-organ damage associated with cell proliferation;

for therapy of metabolic disorders or chronic inflammatory diseases, insulin-dependent and non insulin-dependent diabetes mellitus and their complications (e.g. neuropathy, retinopathy), hyperaldosteronism, bone remodelling, psoriasis, arthritis, rheumatoid arthritis, osteoarthritis sarcoidosis, or eczematous dermatitis;

for the treatment of hepatotoxicity and sudden death, early and advanced liver disease and injury including attendant complication (e.g. hepatotoxicity, fibrosis, cirrhosis), deleterious consequences of tumors such as hypertension resulting from hemangiopericytoma, spastic diseases of the urinary tract and/or bladder, hepatorenal syndrome, immunological diseases involving vasculitis such as lupus, systemic sclerosis, mixed cryoglobulinemia, fibrosis associated with renal dysfunction and hepatotoxicity;

for use in gastrointestinal diseases such as ulcerative colitis, Crohn's disease, gastric mucosal damage, ulcer inflammatory bowel disease and ischemic bowel disease, gall bladder or bile duct-based diseases such as cholangitis, pancreatitis, regulation of cell growth, beginning prostatic hypertrophy, or transplantation, or for use as anti-diarrheal agent;

for the treatment of disorders involving bronchoconstriction or disorders of chronic or acute inflammation such as obstructive pulmonary disease and adult distress syndrome;

for the alleviation of pain including neuropathic pain, peripheral pain and pain associated with cancer such as pain associated with prostate cancer or bone-cancer;

for the treatment of central nervous system vascular disorders such as stroke, transient ischemic attacks, migraine and subarachnoid hemorrhage, central nervous system behavioural disorders, treatment of dementia including Alzheimer's dementia, senile dementia and vascular dementia, epilepsy, or sleep disorders; or for reduction of general morbidity and/or mortality as a result of above utilities.

The present invention also relates to a method for the prevention or treatment of a disease or disorder mentioned herein comprising administering to a subject a pharmaceutically active amount of a compound of formula (I).

Furthermore, the compounds of the formula (I) may also be used favourably in combination with one or more agents selected from lipid lowering agents such as statins, anticoagulants such as coumarins, antithrombotic agents such as clopidogrel, β-blockers, and other cardioprotective agents.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formulae ($I_{CE}$), ($I_{E1}$), and/or ($I_{E2}$) and vice versa.

Preparation of Compounds of Formula (I):

A further aspect of the invention is a process for the preparation of compounds of formulae (I), ($I_{CE}$), ($I_{E1}$), and/or ($I_{E2}$) of the present invention. The compounds obtained may also be converted into pharmaceutically acceptable salts thereof in a manner known per se.

In general, all chemical transformations can be performed according to well-known standard methodologies as described in the literature or as described in the procedures as summarized in Schemes 1 to 4 below. If not indicated otherwise, the generic groups or integers W, $R^1$, $R^2$, $R^3$, $R^4$, $R^5$, $R^6$, $R^7$, $R^8$, p, m and n are as defined for formula (I). Other abbreviations used are defined in the experimental section. In some instances the generic groups W, $R^1$, $R^2$, $R^3$, $R^5$, $R^6$, $R^7$, or $R^8$, might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

Compounds of formula (I), wherein $R^3$ represents —CO—$R^{31}$, are prepared following the procedures outlined in Scheme 1 below. Intermediate II is reduced to the corresponding diol III using standard reducing reagents and conditions such as $LiAlH_4$ and solvents like $Et_2O$ or THF, preferably at temperatures between −20° C. and rt. The primary alcohol group in compounds of formula III is transformed into a leaving group $L^1$ in compound IV, wherein $L^1$ is OTs, OMs, OTf, Cl or Br, using well known methods such as Ts-Cl in the presence of bases such as $NEt_3$, DMAP, and in an adequate solvent such as toluene. Treatment of IV with the appropriate amine $R^4$—NH—B—W in presence of a non-nuclear base such as DIPEA at temperatures between rt and 110° C. gives compounds of formula (I) wherein $R^3$ represents H.

Alcohols of formula (I) wherein $R^3$ represents H can be acylated using standard reagents such as acid chlorides, acid anhydrides, chloroformates, isocyanates, or carbamoylchlorides, if necessary in presence of a Lewis acid such as $MgBr_2$, or in presence of a base such as $NEt_3$ in inert solvents such as DCM or THF at temperatures between 0° C. and rt to give compounds of formula (I) wherein $R^3$ represents —CO—$R^{31}$.

Scheme 1:

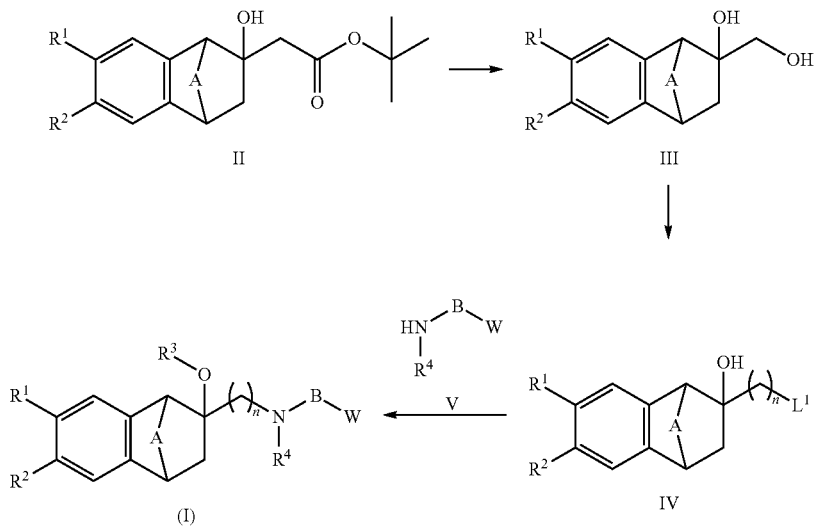

Compounds of formula (I), wherein $R^3$ represents $(C_{1-5})$alkyl, are prepared following the procedures outlined in Scheme 2 below. Protection of the primary OH group in intermediates III with standard O-protecting groups such as TBS or TBDPS applying standard chemistry described in the literature and known to those skilled in the art leads to intermediates VI which can then be O-alkylated with an alkyl halogenide such as MeI in the presence of a base like NaH in a solvent like acetone, DMF or THF at temperatures between 0° C. to rt yielding ethers VII. Deprotection of the primary alcohol using standard deprotection reagents and procedures known to ones skilled in the art (e.g. TBAF in THF for silyl ethers) gives the desired monoalcohols VIII. Transformation of the alcohol group into a leaving group $L^1$ (under the aforementioned conditions) followed by substitution with the appropriate amine $R^4$—NH—B—W as described below leads to compounds of formula (I) wherein $R^3$ represents $(C_{1-5})$alkyl.

Scheme 2:

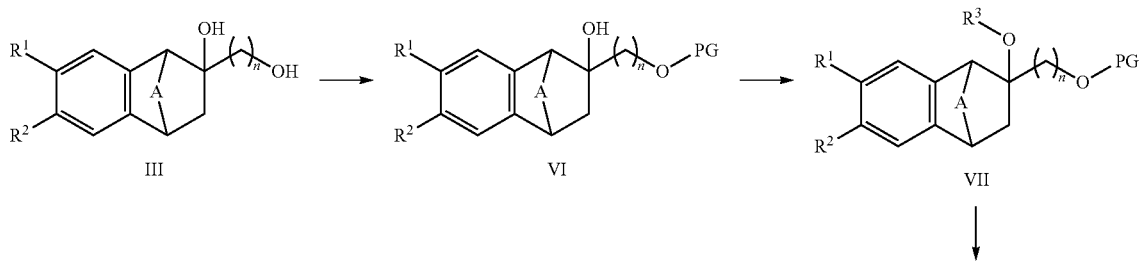

-continued

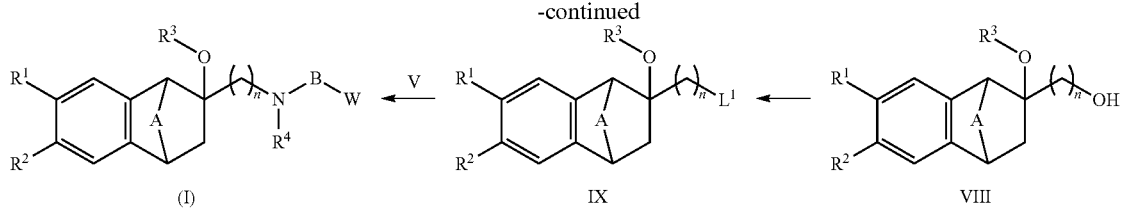

The intermediates II are prepared according to Scheme 3.

A Diels-Alder cycloaddition of 1,4-benzoquinones X, which are commercially available or synthesized according to the methods given in the experimental part below, with 1,3-dienes under either thermal conditions (heating in benzene or DCM) or in the presence of a Lewis acid catalyst such as $BF_3$-dietherate or $AlCl_3$ in an appropriate solvent like DCM, as described by P. A. Crooks, Synth. Comm. 2002, 24, 3813-3819, leads to intermediates XI. Diols XII can be obtained by reducing diones XI under Luche conditions using $CeCl_3$ and a reducing agent like $NaBH_4$ in an appropriate solvent such as MeOH at temperatures around 0° C. Dehydration using $POCl_3$ in pyridine at temperatures between 0° C. and rt leads to compounds of formula XIII. Alcohols XIV can be formed by hydroboration of intermediates XIII using standard conditions such as $BH_3$ in THF. Subsequent oxidation of alcohols XIV using e.g. Dess-Martins-Periodinane in DCM at rt yields ketones of formula XV. Ketones XV are transformed into the desired intermediates II wherein n≧2 by addition of nucleophiles such as Grignard reagents or lithiated alkyl groups such as lithiated tert.-butylacetate (prepared in situ using tert.-butyl acetate, n-butyllithium and DIPA at temperatures of −50° C. in an adequate mixture of solvents such as toluene-THF or hexane-THF) at temperatures between −50° C. and rt. Intermediates II wherein n=1 can be obtained by hydrocyanation of ketone derivatives XV under standard conditions using e.g. KCN or TMSCN in appropriate solvents like MeCN or DCM at rt to get intermediates XVI followed by hydrolysis under standard acidic conditions in the presence of an alcohol such as tert.-BuOH.

Scheme 3:

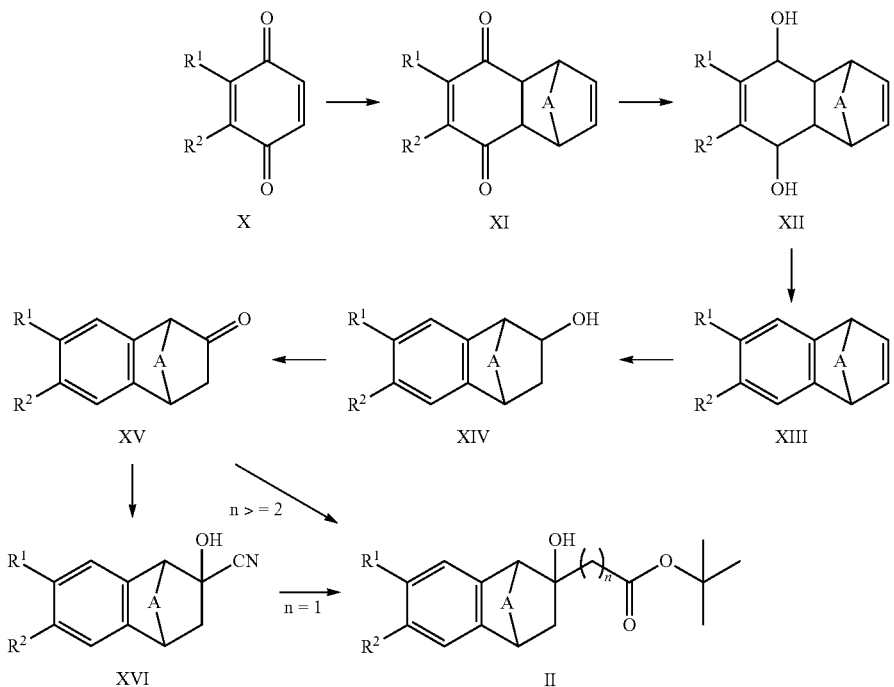

The amino building blocks $R^4$—NH—B—W can be prepared according to the description below in Scheme 4.

A suitably substituted dianiline derivative XVII, which is commercially available or synthesized according to the methods given in the experimental part below, is coupled to an accordingly protected N-alkylamino-alkanoic acid derivative, which is commercially available or synthesized following known literature procedures, using standard coupling reagents and conditions such as EDC/HOBt in presence of a base such as DIPEA, in solvents like THF at rt to give the aniline derivatives XVIII. Heating of XVIII, preferably under microwave conditions to about 150° C., neat or in appropriate solvents such as toluene preferably in the presence of TsOH or acetic acid leads to the protected aminoalkyl benzimidazole derivatives XIX. Optionally, in case $R^5$ is ($C_{1-5}$)alkyl, the substituent can be introduced using standard reactions such as alkylation with an appropriate alkyl halogenide in presence of a base like NaH or $K_2CO_3$ in a solvent like acetone, DMF or THF at temperatures of about 0° C. Deprotection using standard deprotection reagents and procedures known to the ones skilled in the art (hydrogen for PG=Cbz, TFA or HCl for PG=BOC) gives the desired aminoalkyl benzimidazole derivatives V.

Scheme 4:

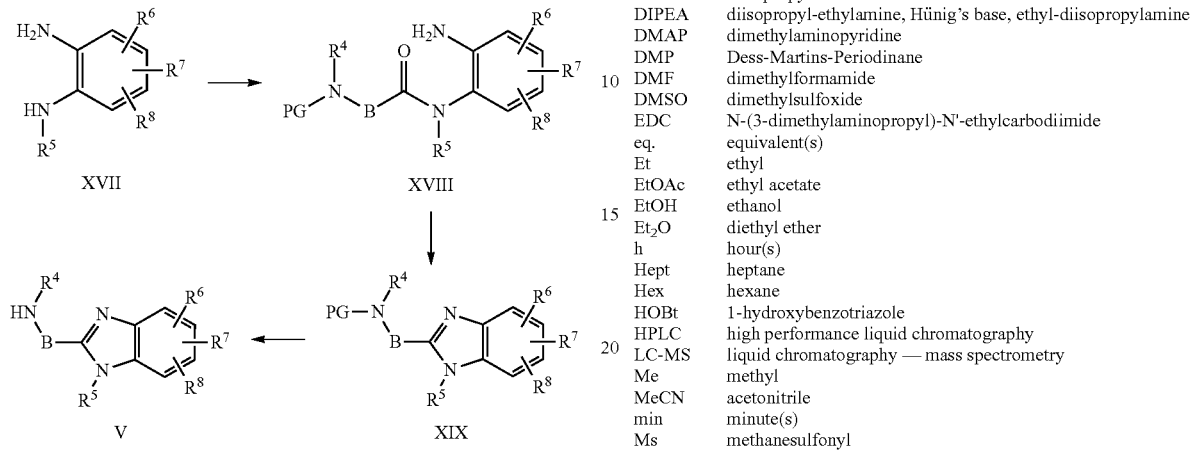

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as NEt₃, diethylamine) and eluent B (hexane), at a flow rate of 0.8 to 150 mL/min.

Experimental Part

The following examples illustrate the invention but do not at all limit the scope thereof.

All temperatures are stated in ° C. Compounds are characterized by $^1$H-NMR (300 MHz, 400 MHz) or $^{13}$C-NMR (100 MHz) (Bruker/Varian; chemical shifts are given in ppm relative to the solvent used; multiplicities: s=singlet, d=doublet, t=triplet, q=quartett, p=pentuplet, hex=hexet, hept=heptet, m=multiplet, br=broad, coupling constants are given in Hz); by LC-MS (system A) Finnigan Navigator with HP 1100 Binary Pump and DAD, column: 4.6×50 mm, Zorbax SB-AQ, 5 μm, 120 Å, gradient: 5-95% MeCN in water, 1 min, with 0.04% TFA, flow: 4.5 mL/min or by LC-MS (system B) column: X-terra® MS C18, 2.1×50 mm, 5 μm, gradient: 5-95% MeCN in water, 1 min, with 0.06% formic acid, flow: 3 ml/min, $t_R$ is given in min; by TLC (TLC-plates from Merck, Silica gel 60 F$_{254}$); or by melting point. Compounds are purified by preparative HPLC (column: X-terra RP18, 50×19 mm, 5 μm, gradient: 10-95% MeCN in water containing 0.5% of formic acid) or by column chromatography on silica gel. Racemates can be separated into their enantiomers by preparative HPLC (preferred conditions: specified below).

Abbreviations: (as Used Herein or in the Description Above)

| aq. | aqueous |
|---|---|
| Ac | acetyl |
| AcOH | acetic acid |
| anh. | anhydrous |
| BOC | tert.-butoxycarbonyl |
| BSA | bovine serum albumin |
| Bu | butyl |
| Cbz | benzyloxycarbonyl |
| CC | column chromatography on silica gel |
| DCM | dichloromethane |
| dil. | diluted |
| DIPA | diisopropylamine |
| DIPEA | diisopropyl-ethylamine, Hünig's base, ethyl-diisopropylamine |
| DMAP | dimethylaminopyridine |
| DMP | Dess-Martins-Periodinane |
| DMF | dimethylformamide |
| DMSO | dimethylsulfoxide |
| EDC | N-(3-dimethylaminopropyl)-N'-ethylcarbodiimide |
| eq. | equivalent(s) |
| Et | ethyl |
| EtOAc | ethyl acetate |
| EtOH | ethanol |
| Et₂O | diethyl ether |
| h | hour(s) |
| Hept | heptane |
| Hex | hexane |
| HOBt | 1-hydroxybenzotriazole |
| HPLC | high performance liquid chromatography |
| LC-MS | liquid chromatography — mass spectrometry |
| Me | methyl |
| MeCN | acetonitrile |
| min | minute(s) |
| Ms | methanesulfonyl |
| NEt₃ | triethylamine |
| OAc | O-acetyl, acetate |
| Pd/C | palladium on carbon |
| prep. | preparative |
| PyBOP | benzotriazole-1-yl-oxy-tris-pyrrolidino-phosphonium hexafluorophosphate |
| rt | room temperature |
| sat. | saturated |
| tert.- | tertiary (tert.-butyl = t-butyl = tertiary butyl) |
| TBAF | tetra-n-butylammonium fluoride |
| TBDPS | tert.-butyldiphenylsilyl |
| TBS | tert.-butyldimethylsilyl |
| Tf | trifluoromethanesulfonyl |
| TFA | trifluoroacetic acid |
| THF | tetrahydrofuran |
| TLC | thin layer chromatography |
| TMS | trimethylsilyl |
| $t_R$ | retention time |
| Ts | para-toluenesulfonyl |

PREPARATION OF EXAMPLES

Example 1 rac-(1R*,8R*,9R*)-9-(2-{[3-(1H-Benzoimidazol-2-yl)-propyl]-methyl-amino}-ethyl)-tricyclo[6.2.2.0$^{2,7}$]dodeca-2,4,6-trien-9-ol 1.1 Tricyclo[6.2.2.0$^{2,7}$]dodeca-4,9-diene-3,6-dione A solution of 40 g of 1,4-benzoquinone and 35 mL of 1,3-cyclohexadiene in 90 mL of benzene was stirred in a closed vessel for 3 days at rt. The reaction mixture was concentrated and the residue was crystallized in EtOH to obtain 57 g of the desired compound as mixture of stereoisomers as greenish solid.

$^1$H-NMR ((CD₃)₂SO): 6.70 (s, 2H); 6.18 (m, 2H); 3.03 (m, 4H); 1.65 (m, 2H); 1.20 (m, 2H).

1.2 Tricyclo[6.2.2.0$^{2,7}$]dodeca-4,9-diene-3,6-diol

To a solution of 25.6 g of tricyclo[6.2.2.0$^{2,7}$]dodeca-4,9-diene-3,6-dione in 600 mL of MeOH were added 58.0 g of CeCl₃ 7H₂O. Then, 5.7 g of NaBH₄ were portionwise added at 0° C. and the mixture was stirred for 1 h at the same temperature. After evaporation of the solvent the residue was redissolved in EtOAc, it was washed with $H_2O$, dried over $MgSO_4$ and concentrated in vacuo. The crude was again redissolved in EtOAc and triturated with Hept to obtain 27.9 g of the desired compound as mixture of stereoisomers as brownish solid.

LC-MS (A): $t_R$=0.73 min; $[M-H_2O+H]^+$: 175.21

1.3 rac-(1R*,8S*)-Tricyclo[6.2.2.0$^{2,7}$]dodeca-2,4,6,9-tetraene

To a solution of 27.9 g of tricyclo[6.2.2.0$^{2,7}$]dodeca-4,9-diene-3,6-diol in 165 mL of pyridine were portionwise added 30 mL of $POCl_3$ at 0° C. The reaction was stirred for 3 days at rt before it was quenched by careful addition of ice under cooling. The resulting mixture was extracted with Hept (4×50 mL). The combined organic phases were washed with $H_2O$, 15% HCl solution and again with $H_2O$. The organic phase was dried over $MgSO_4$ and concentrated in vacuo to obtain 10.6 g of the desired compound as yellow oil.

$^1$H-NMR (($CD_3$)$_2$SO): 7.18 (m, 2H); 7.02 (m, 2H); 6.48 (m, 2H); 3.97 (s, 2H); 1.43 (m, 2H); 1.25 (m, 2H).

1.4 (9RS)-(1R*,8S*)-Tricyclo[6.2.2.0$^{2,7}$]dodeca-2,4,6-trien-9-ol

A solution of 15.8 g of tricyclo[6.2.2.0$^{2,7}$]dodeca-2,4,6,9-tetraene in 42 mL of THF was added to 82 mL of 1M $BH_3$ in THF at 0° C. The reaction mixture was stirred overnight while the temperature reached rt. The reaction was quenched by addition of 40 mL of 0.3N NaOH solution followed by 134 mL of a 35% $H_2O_2$ solution. The mixture was extracted with $Et_2O$, washed with $H_2O$, dried over $MgSO_4$ and concentrated in vacuo to obtain 17.7 g of the desired compound as yellow oil.

LC-MS (A): $t_R$=0.84 min; $[M-H_2O+H]^+$: 157.19

1.5 rac-(1R*,8R*)-Tricyclo[6.2.2.0$^{2,7}$]dodeca-2,4,6-trien-9-one

To a solution of 5.6 g of tricyclo[6.2.2.0$^{2,7}$]dodeca-2,4,6-trien-9-ol in 30 mL of DCM were added 110 mL of a 15% DMP solution in DCM. After stirring overnight 300 mL of EtOAc/Hept (1:1) were added, the obtained suspension was filtered over a pad of celite and the filtrated was concentrated in vacuo. The residue was treated again with EtOAc/Hept (1:1) and filtered over celite. This procedure was repeated twice to obtain 4.9 g of the desired compound as yellow oil.

LC-MS (A): $t_R$=0.88 min; $[M+H+CH_3CN]^+$: 214.19

1.6 rac-(1R*,8R*,9R*)-(9-Hydroxy-tricyclo[6.2.2.0$^{2,7}$]dodeca-2,4,6-trien-9-yl)-acetic acid tert-butyl ester and rac-(1R*,8R*,9S*)-(9-hydroxy-tricyclo[6.2.2.0$^{2,7}$]dodeca-2,4,6-trien-9-yl)-acetic acid tert-butyl ester To a solution of 3.5 mL of DIPA in 6 mL THF were added dropwise 9.9 mL of n-butyllithium (2.5M in Hept) at −20° C. After 20 min, 12 mL of toluene were added and the solution was stirred for 30 min. The mixture was cooled to −50° C., 4.5 mL of tert.-butyl acetate were added and stirring was continued for 1 h at −50° C. Then, 2.5 g of rac-(1R*,8R*)-tricyclo[6.2.2.0$^{2,7}$]dodeca-2,4,6-trien-9-one dissolved in 6 mL of toluol were added and the solution was stirred at −50 to −20° C. over 2.5 h. The reaction mixture was poured on ice/aq. HCl, the organic phase was separated, washed with sat. aq. $NaHCO_3$, dried over $Na_2SO_4$ and concentrated in vacuo. The crude reaction product was purified by CC with Hept/EtOAc (4:1) to yield 2.6 g of the major racemate, rac-(1R*,8R*,9R*)-(9-hydroxy-tricyclo[6.2.2.0$^{2,7}$]dodeca-2,4,6-trien-9-yl)-acetic acid tert-butyl ester as beige solid and 0.4 g of the minor racemate, rac-(1R*,8R*,9S*)-(9-hydroxy-tricyclo[6.2.2.0$^{2,7}$]dodeca-2,4,6-trien-9-yl)-acetic acid tert-butyl ester as yellow oil.

LC-MS (A), (major racemate): $t_R$=1.04 min; $[M+H]^+$: 288.85

LC-MS (A), (minor racemate): $t_R$=1.03 min; $[M+H]^+$: 289.20

1.7 rac-(1R*,8R*,9R*)-9-(2-Hydroxy-ethyl)-tricyclo[6.2.2.0$^{2,7}$]dodeca-2,4,6-trien-9-ol A solution of 2.6 g of rac-(1R*,8R*,9R*)-(9-hydroxy-tricyclo[6.2.2.0$^{2,7}$]dodeca-2,4,6-trien-9-yl)-acetic acid tert-butyl ester in 10 mL of THF was added to 15.3 mL of a 1M $LiAlH_4$ solution in THF at −10° C. The mixture was stirred for 4 h while the temperature reached slowly 0° C. The reaction was quenched by addition of a 15% aq. NaOH solution. The mixture was diluted with EtOAc, washed with $H_2O$, dried over $MgSO_4$ and concentrated in vacuo to obtain 1.6 g of the desired compound as white solid.

LC-MS (A): $t_R$=0.78 min; $[M-H_2O+H]^+$: 201.15

1.8 (1S,8S,9S)-9-(2-Hydroxy-ethyl)-tricyclo[6.2.2.0$^{2,7}$]dodeca-2,4,6-trien-9-ol and (1R,8R,9R)-9-(2-hydroxy-ethyl)-tricyclo[6.2.2.0$^{2,7}$]dodeca-2,4,6-trien-9-ol rac-(1R*,8R*,9R*)-9-(2-Hydroxy-ethyl)-tricyclo[6.2.2.0$^{2,7}$]dodeca-2,4,6-trien-9-ol was separated into the respective enantiomers using prep. chiral HPLC (column: Chiralcel OD 20×250 mm, 10 um; Hex/EtOH 95:5, flow 16 mL/min).

Chiral analytic HPLC (Chiralcel OD 4.6×250 mm, 10 um; Hex/EtOH 95:5, flow 0.8 mL/min).

Enantiomer A: $t_R$=9.98 min.

Enantiomer B: $t_R$=11.31 min.

1.9 rac-Toluene-4-sulfonic acid (1R*,8R*,9R*)-2-(9-hydroxy-tricyclo[6.2.2.0$^{2,7}$]dodeca-2,4,6-trien-9-yl)-ethyl ester A mixture of 2.0 g of rac-(1R*,8R*,9R*)-9-(2-hydroxy-ethyl)-tricyclo[6.2.2.0$^{2,7}$]dodeca-2,4,6-trien-9-ol, 1.9 g of TsCl, 1.5 mL of $NEt_3$ and 0.22 g of DMAP in 120 mL of toluene was stirred overnight at rt. The reaction mixture was quenched with water, the organic phase was separated, washed with brine, dried over $MgSO_4$ and concentrated in vacuo. The residue was purified by CC with Hept/EtOAc (1:1) to yield 2.7 g of the desired compound as yellow oil.

LC-MS (A): $t_R$=1.03 min; $[M-H_2O+H]^+$: 355.05

1.10 rac-(1R*,8R*,9R*)-9-(2-{[3-(1H-Benzoimidazol-2-yl)-propyl]-methyl-amino}-ethyl)-tricyclo[6.2.2.0$^{2,7}$]dodeca-2,4,6-trien-9-ol A mixture of 1000 mg of rac-toluene-4-sulfonic acid (1R*,8R*,9R*)-2-(9-hydroxy-tricyclo[6.2.2.0$^{2,7}$]dodeca-2,4,6-trien-9-yl)ethyl ester and 508 mg of [3-(1H-benzoimidazol-2-yl)-propyl]-methyl-amine in 2 mL of DIPEA was heated to 110° C. for 30 min. The reaction mixture was cooled to rt, quenched with MeOH-water and extracted with EtOAc. The organic phase was separated, dried over $Na_2SO_4$ and concentrated in vacuo to obtain 1.0 g as beige solid. A part of the crude product was purified by CC with EtOAc/MeOH (2:1) to obtain the desired compound as beige foam.

LC-MS (A): $t_R$=0.67 min; $[M+H]^+$: 390.35.

Example 1A rac-Methoxy-acetic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester 1A.1 rac-Methoxy-acetic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester To a solution of 250 mg of rac-(1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-ol in 10 mL of toluol and 0.1 mL of NEt$_3$ were added 0.1 mL of methoxyacetyl chloride at 0° C. The reaction mixture was stirred for 2 h at rt and then quenched with sat. aq. NaHCO$_3$. The product was extracted with EtOAc, dried over Na$_2$SO$_4$ and concentrated in vacuo. Purification by CC with EtOAc/MeOH (1:1) yielded 130 mg of the desired compound as beige foam.

LC-MS (A): $t_R$=0.71 min; [M+H]$^+$: 462.21.

1A.2 rac-Methoxy-acetic acid (1R*,8R*,9R*)-9-(2-{[3-(1H-benzoimidazol-2yl)-propyl]-methyl-amino}-ethyl)-tricyclo[6.2.2.0$^{2,7}$]dodeca-2,4,6-trien-9-yl ester dihydrochloride The above product may be transformed into the corresponding dihydrochloride salt using the following procedure.

130 mg of rac-methoxy-acetic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester were dissolved in 2 mL EtOAc, the solution was cooled with an ice bath and 2 mL of 1.5N HCl in EtOAc was added. The reaction mixture was evaporated to dryness without heating to give the desired compound as dihydrochloride.

Example 1B rac-Isobutyric acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester This compound was prepared using a method analogous to that of example 1A, step 1.A1, isobutyrylchloride replacing methoxyacetyl chloride.

LC-MS (A): $t_R$=0.78 min; [M+H]$^+$: 460.28.

Example 1C rac-Cyclopropanecarboxylic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester This compound was prepared using a method analogous to that of example 1A, step 1.A1, cyclopropanecarbonyl chloride replacing methoxyacetyl chloride.

LC-MS (A): $t_R$=0.77 min; [M+H]$^+$: 458.27.

Example 2

(1S,8S,9S)-9-(2-{[3-(1H-Benzoimidazol-2-yl)-propyl]-methyl-amino}-ethyl)-tricyclo[6.2.2.0$^{2,7}$]dodeca-2,4,6-trien-9-ol or (1R,8R,9R)-9-(2-{[3-(1H-benzoimidazol-2-yl)-propyl]-methyl-amino}-ethyl)-tricyclo[6.2.2.0$^{2,7}$]dodeca-2,4,6-trien-9-ol Prepared according to procedures analogous to that of example 1, steps 1.9 and 1.10, using enantiomer A of rac-(1R*,8R*,9R*)-9-(2-hydroxy-ethyl)-tricyclo[6.2.2.0$^{2,7}$]dodeca-2,4,6-trien-9-ol (intermediate 1.8) in step 1.9.

LC-MS (A): $t_R$=0.71 min; [M+H]$^+$: 390.17.

Example 2A

Isobutyric acid (1S,8S,9S)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester or isobutyric acid (1R,8R,9R)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester This compound was prepared using a method analogous to that of example 1A, step 1.A1, the compound of example 2 replacing the compound of example 1 and isobutyrylchloride replacing methoxyacetyl chloride.

LC-MS (A): $t_R$=0.82 min; [M+H]$^+$: 460.64.

Example 3

(1S,8S,9S)-9-(2-{[3-(1H-Benzoimidazol-2-yl)-propyl]-methyl-amino}-ethyl)-tricyclo[6.2.2.0$^{2,7}$]dodeca-2,4,6-trien-9-ol or (1R,8R,9R)-9-(2-{[3-(1H-benzoimidazol-2-yl)-propyl]-methyl-amino}-ethyl)-tricyclo[6.2.2.0$^{2,7}$]dodeca-2,4,6-trien-9-ol Prepared according to procedures analogous to that of example 1, steps 1.9 and 1.10, using enantiomer B of rac-(1R*,8R*,9R*)-9-(2-hydroxy-ethyl)-tricyclo[6.2.2.0$^{2,7}$]dodeca-2,4,6-trien-9-ol (intermediate 1.8) in step 1.9.

LC-MS (A): $t_R$=0.72 min; [M+H]$^+$: 390.44.

Example 4 rac-(1R*,8R*,9R*)-[3-(1H-Benzoimidazol-2-yl)-propyl]-[2-(9-methoxy-tricyclo[6.2.2.0$^{2,7}$]dodeca-2,4,6-trien-9-yl)-ethyl]-methyl-amine 4.1 rac-(1R*,8R*,9R*)-9-[2-(tert-Butyl-dimethyl-silanyloxy)-ethyl]-tricyclo[6.2.2.0$^{2,7}$]dodeca-2,4,6-trien-9-ol A mixture of 200 mg of rac-(1R*,8R*,9R*)-9-(2-hydroxy-ethyl)-tricyclo[6.2.2.0$^{2,7}$]dodeca-2,4,6-trien-9-ol, 138 mg of TBSCl and 62 mg of imidazole in 2 mL of DCM was stirred overnight at rt. The reaction was quenched with H$_2$O, the organic phase was washed with brine, dried over Na$_2$SO$_4$ and concentrated in vacuo to yield 300 mg of the desired compound as yellow oil.

LC-MS (A): $t_R$=1.16 min; [M+H]$^+$: 333.20.

4.2 rac-(1R*,8R*,9R*)-2-(9-Methoxy-tricyclo[6.2.2.0$^{2,7}$]dodeca-2,4,6-trien-9-yl)-ethanol To a solution of 135 mg of rac-(1R*,8R*,9R*)-9-[2-(tert-butyl-dimethyl-silanyloxy)-ethyl]-tricyclo[6.2.2.0$^{2,7}$]dodeca-2,4,6-trien-9-ol in 2 mL of THF were added 29 mg of NaH (60%, oil dispersion) followed by 74 uL of MeI at 0° C. The ice bath was removed after 10 min and the mixture was stirred overnight at rt. The yellow suspension was carefully quenched with $H_2O$, extracted with EtOAc, washed with brine, dried over $Na_2SO_4$ and then concentrated in vacuo to obtain 98 mg of a yellow oil. The crude product was then dissolved in 2 mL of THF, 0.2 mL of 1M TBAF in THF was added and the mixture was stirred overnight at rt. The reaction mixture was quenched with $H_2O$, extracted with EtOAc, dried over $Na_2SO_4$ and concentrated in vacuo. Purification by CC with Hept/EtOAc (4:1) yielded 56 mg of the desired compound as yellow oil.

$^1$H-NMR (CD$_3$OD): 7.13 (m, 4H); 3.50 (m, 2H); 3.22 (s, 3H); 3.08 (m, 1H); 2.95 (m, 1H); 2.08 (m, 1H); 1.80 (m, 1H); 1.65 (m, 1H); 1.43 (m, 1H); 1.33 (m, 2H); 1.12 (m, 2H).

4.3 rac-(1R*,8R*,9R*)-[3-(1H-Benzoimidazol-2-yl)-propyl-][-2-(9-methoxy-tricyclo[6.2.2.0$^{2,7}$]dodeca-2,4,6-trien-9-yl)-ethyl]-methyl-amine Prepared according to procedures analogous to that of example 1, steps 1.9 and 1.10, intermediate 4.2 replacing intermediate 1.7 in step 1.9.

LC-MS (A): $t_R$=0.75 min; [M+H]$^+$: 404.21

Example 5 rac-(1R*,8R*,9S*)-9-(2-{[3-(1H-Benzoimidazol-2-yl)-propyl]-methyl-amino}-ethyl)-tricyclo[6.2.2.0$^{2,7}$]dodeca-2,4,6-trien-9-ol Prepared according to procedures analogous to that of example 1, steps 1.7 to 1.10, rac-(1R*,8R*,9S*)-(9-hydroxy-tricyclo[6.2.2.0$^{2,7}$]dodeca-2,4,6-trien-9-yl)-acetic acid tert-butyl ester replacing rac-(1R*,8R*,9R*)-(9-hydroxy-tricyclo[6.2.2.0$^{2,7}$]dodeca-2,4,6-trien-9-yl)-acetic acid tert-butyl ester in step 1.7.

LC-MS (A): $t_R$=0.65 min; [M+H]$^+$: 390.39

Example 5A rac-Isobutyric acid (1R*,8R*,9S*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester This compound was prepared using a method analogous to that of example 1A, step 1.A1, the compound of example 5 replacing the compound of example 1 and isobutyrylchloride replacing methoxyacetyl chloride.

LC-MS (A): $t_R$=0.76 min; [M+H]$^+$: 460.31

Example 6 rac-(1R*,8R*,9R*)-9-{2-[4-(1H-Benzoimidazol-2-yl)-piperidin-1-yl]-ethyl}-tricyclo[6.2.2.0$^{2,7}$]dodeca-2,4,6-trien-9-ol 6.1 4-(2-Amino-phenylcarbamoyl)-piperidine-1-carboxylic acid benzyl ester A mixture of 3.5 g of piperidine-1,4-dicarboxylic acid monobenzyl ester, 1.5 g of phenylendiamine, 2.3 mL of DIPEA and 6.9 g of PyBOP in 40 mL of DCM was stirred overnight at rt. The reaction was quenched with $H_2O$, extracted with DCM, dried over MgSO$_4$ and concentrated in vacuo to obtain 10 g of the desired compound as crude brown solid.

LC-MS (A): $t_R$=0.76 min; [M+H]$^+$: 354.26.

6.2 4-(1H-Benzoimidazol-2-yl)-piperidine-1-carboxylic acid benzyl ester

A solution of crude 10 g of 4-(2-amino-phenylcarbamoyl)-piperidine-1-carboxylic acid benzyl ester was dissolved in 200 mL glacial AcOH and heated to 90° C. for 1.5 h. The reaction mixture was evaporated to dryness, redissolved in 20 mL MeOH and concentrated in vacuo. Purification by CC with EtOAc/Hept (9:1) to EtOAc yielded 1.3 g of the desired compound as beige solid.

LC-MS (B): $t_R$=0.78 min; [M+H]$^+$: 336.12.

6.3 2-Piperidin-4-yl-1H-benzoimidazole

Dissolved 1.3 g of 4-(1H-benzoimidazol-2-yl)-piperidine-1-carboxylic acid benzyl ester in 40 mL degassed EtOH. Added 200 mg of 10 wt % Pd/C and stirred the mixture under a $H_2$ atmosphere for 4 h at rt. The reaction mixture was then filtered over a pad of celite and washed with EtOH. Concentration in vacuo afforded 0.85 g of the desired compound as beige solid.

LC-MS (A): $t_R$=0.30 min; [M+H]$^+$: 202.14.

6.4 rac-(1R*,8R*,9R*)-9-{2-[4-(1H-Benzoimidazol-2-yl)-piperidin-1-yl]-ethyl}-tricyclo[6.2.2.0$^{2,7}$]dodeca-2,4,6-trien-9-ol This compound was prepared using a method analogous to that of example 1, step 1.10, intermediate 6.3 replacing [3-(1H-benzoimidazol-2-yl)-propyl]-methyl-amine.

LC-MS (A): $t_R$=0.65 min; [M+H]$^+$: 402.32

Example 6A rac-Isobutyric acid (1R*,8R*,9R*)-9-{2-[4-(1H-benzoimidazol-2-yl)-piperidin-1-yl]-ethyl}-tricyclo[6.2.2.0$^{2,7}$]dodeca-2,4,6-trien-9-yl ester This compound was prepared using a method analogous to that of example 1A, step 1.A1, the compound of example 6 replacing the compound of example 1 and isobutyrylchloride replacing methoxyacetyl chloride.

LC-MS (A): $t_R$=0.74 min; [M+H]$^+$: 472.37

Example 7

(1R*,8R*,9R*)-9-{2-[(3RS)-3-(1H-Benzoimidazol-2-yl)-piperidin-1-yl]-ethyl}-tricyclo[6.2.2.0$^{2,7}$]dodeca-2,4,6-trien-9-ol 7.1 2-Piperidin-3-yl-1H-benzoimidazole Prepared according to procedures analogous to that of example 6, steps 6.1 to 6.3, piperidine-1,3-dicarboxylic acid monobenzyl ester replacing piperidine-1,4-dicarboxylic acid monobenzyl ester in step 6.1.

LC-MS (A): $t_R$=0.34 min; [M+H]$^+$: 202.14

7.2 (1R*,8R*,9R*)-9-{2-[(3RS)-3-(1H-Benzoimidazol-2-yl)-piperidin-1-yl]-ethyl}-tricyclo[6.2.2.0$^{2,7}$]dodeca-2,4,6-trien-9-ol This compound was prepared using a method analogous to that of example 1, step 1.10, intermediate 7.1 replacing [3-(1H-benzoimidazol-2-yl)-propyl]-methyl-amine.

LC-MS (A): $t_R$=0.73 min; [M+H]$^+$: 402.04

Example 7A

Isobutyric acid (1R*,8R*,9R*)-9-{2-[(3RS)-3-(1H-benzoimidazol-2-yl)-piperidin-1-yl]-ethyl}-tricyclo[6.2.2.0$^{2,7}$]dodeca-2,4,6-trien-9-yl ester This compound was prepared using a method analogous to that of example 1A, step 1.A1, the compound of example 7 replacing the compound of example 1 and isobutyrylchloride replacing methoxyacetyl chloride.
LC-MS (A): $t_R$=0.85 min; [M+H]$^+$: 472.82

Example 8 rac-(1R*,8R*,9R*)-9-{2-[4-(1H-Benzoimidazol-2-yl)-4-phenyl-piperidin-1-yl]-ethyl}-tricyclo[6.2.2.0$^{2,7}$]dodeca-2,4,6-trien-9-ol

8.1 2-(4-Phenyl-piperidin-4-yl)-1H-benzoimidazole

Prepared according to procedures analogous to that of example 6, steps 6.1 to 6.3, 4-phenyl-piperidine-1,4-dicarboxylic acid monobenzyl ester replacing piperidine-1,4-dicarboxylic acid monobenzyl ester in step 6.1.
LC-MS (A): $t_R$=0.57 min; [M+H]$^+$: 278.22

8.2 rac-(1R*,8R*,9R*)-9-{2-[4-(1H-Benzoimidazol-2-yl)-4-phenyl-piperidin-1-yl]-ethyl}-tricyclo[6.2.2.0$^{2,7}$]dodeca-2,4,6-trien-9-ol This compound was prepared using a method analogous to that of example 1, step 1.10, intermediate 8.1 replacing [3-(1H-benzoimidazol-2-yl)-propyl]-methyl-amine.
LC-MS (A): $t_R$=0.75 min; [M+H]$^+$: 478.19

Example 8A rac-Isobutyric acid (1R*,8R*,9R*)-9-{2-[4-(1H-benzoimidazol-2-yl)-4-phenyl-piperidin-1-yl]-ethyl}-tricyclo[6.2.2.0$^{2,7}$]dodeca-2,4,6-trien-9-yl ester This compound was prepared using a method analogous to that of example 1A, step 1.A1, the compound of example 8 replacing the compound of example 1 and isobutyrylchloride replacing methoxyacetyl chloride.
LC-MS (A): $t_R$=0.86 min; [M+H]$^+$: 548.19

Example 9 rac-(1R*,8R*,9R*)-9-(2-{[3-(1H-Benzoimidazol-2-yl)-propyl]-methyl-amino}-ethyl)-4,5-difluoro-tricyclo[6.2.2.0$^{2,7}$]dodeca-2,4,6-trien-9-ol

9.1 4,5-Difluoro-tricyclo[6.2.2.0$^{2,7}$]dodeca-4,9-diene-3,6-dione

A solution of 1.7 g of 2,3-difluoro-1,4-benzoquinone (G. Haufe, Perkin Transactions 1 (2002), (23), 2719-2728), 2.2 mL of 1,3 cyclohexadiene in 25 mL of Et$_2$O was heated in a closed vessel at 50° C. for 2 h. After cooling to rt the mixture was concentrated in vacuo to obtain 1.4 g of the desired compound as mixture of stereoisomers as yellow solid.
$^1$H-NMR (DMSO): 6.20 (s, 2H); 3.18 (s, 2H); 3.03 (s, 2H); 1.71 (m, 2H); 1.21 (m, 2H).

9.2 rac-(1R*,8R*,9R*)-9-(2-{[3-(1H-Benzoimidazol-2-yl)-propyl]-methyl-amino}-ethyl)-4,5-difluoro-tricyclo[6.2.2.0$^{2,7}$]dodeca-2,4,6-trien-9-ol Prepared according to procedures analogous to that of example 1, steps 1.2 to 1.10, 4,5-difluoro-tricyclo[6.2.2.0$^{2,7}$]dodeca-4,9-diene-3,6-dione (step 9.1) replacing tricyclo[6.2.2.0$^{2,7}$]dodeca-4,9-diene-3,6-dione (step 1.1) in step 1.2.
LC-MS (A): $t_R$=0.70 min; [M–H$_2$O+H]$^+$: 426.04

Example 9A rac-Isobutyric acid (1R*,8R*,9R*)-9-(2-{[3-(1H-benzoimidazol-2-yl)-propyl]-methyl-amino}-ethyl)-4,5-difluoro-tricyclo[6.2.2.0$^{2,7}$]dodeca-2,4,6-trien-9-yl ester This compound was prepared using a method analogous to that of example 1A, step 1.A1, the compound of example 9 replacing the compound of example 1 and isobutyrylchloride replacing methoxyacetyl chloride.
LC-MS (B): $t_R$=0.78 min; [M+H]$^+$: 496.13.

Example 10 rac-(1R*,8R*,12R*)-12-(2-{[3-(1H-Benzoimidazol-2-yl)-propyl]-methyl-amino}-ethyl)-tricyclo[6.3.2.0$^{2,7}$]trideca-2,4,6-trien-12-ol

10.1 Tricyclo[6.3.2.0$^{2,7}$]trideca-4,12-diene-3,6-dione

To a solution of 17.2 g of 1,4-benzoquinone in 240 mL DCM were added 7.6 mL of BF$_3$-diethyletherate followed by 17.2 mL of 1,3-cycloheptadiene at –20° C. The cooling bath was removed after 20 min and the mixture furthermore stirred for 30 min at rt. The reaction mixture was then poured into ice cold KOH (30% aq.) solution and it was vigorously stirred for 10 min. After filtration over celite the organic phase was dried over K$_2$CO$_3$ and concentrated in vacuo to obtain 21.7 g of the desired compound as mixture of stereoisomers as brown solid.
$^1$H-NMR (CD$_3$OD): 6.71 (s, 2H); 6.04 (m, 2H); 3.02 (m, 2H); 1.65 (m, 8H).

10.2 rac-(1R*,8R*,12R*)-12-(2-Hydroxy-ethyl)-tricyclo[6.3.2.0$^{2,7}$]trideca-2,4,6-trien-12-ol Prepared according to procedures analogous to that of example 1, steps 1.2 to 1.7, tricyclo[6.3.2.0$^{2,7}$]trideca-4,12-diene-3,6-dione (step 10.1) replacing tricyclo[6.2.2.0$^{2,7}$]dodeca-4,9-diene-3,6-dione (step 1.1) in step 1.2.
LC-MS (A): $t_R$=0.83 min; [M+Na+H]$^+$: 256.23

10.3 (1S,8S,12S)-12-(2-Hydroxy-ethyl)-tricyclo[6.3.2.0$^{2,7}$]trideca-2,4,6-trien-12-ol and (1R,8R,12R)-12-(2-hydroxy-ethyl)-tricyclo[6.3.2.0$^{2,7}$]trideca-2,4,6-trien-12-ol rac-(1R*,8R*,12R*)-12-(2-Hydroxy-ethyl)-tricyclo[6.3.2.0$^{2,7}$]trideca-2,4,6-trien-12-ol was separated into the respective enantiomers using prep. chiral HPLC (column: Chiralcel OJ 250×4.6 mm, 20 um; Hept/EtOH 95:5, flow 2.0 mL/min).
Chiral analytic HPLC (Chiralcel OD 4.6×250 mm, 10 um; Hex/EtOH 95:5, flow 0.8 mL/min).
Enantiomer A: $t_R$=9.43 min.
Enantiomer B: $t_R$=10.58 min.

10.4 rac-(1R*,8R*,12R*)-12-(2-{[3-(1H-Benzoimidazol-2-yl)-propyl]-methyl-amino}-ethyl)-tricyclo[6.3.2.0$^{2,7}$]trideca-2,4,6-trien-12-ol Prepared according to procedures analogous to that of example 1, steps 1.9 to 1.10, rac-(1R*,8R*,12R*)-12-(2-hydroxy-ethyl)-tricyclo[6.3.2.0$^{2,7}$]trideca-2,4,6-trien-12-ol replacing rac-(1R*,8R*,9R*)-9-(2-hydroxy-ethyl)-tricyclo[6.2.2.0$^{2,7}$]dodeca-2,4,6-trien-9-ol in step 1.9.

LC-MS (A): $t_R$=0.75 min; [M+H]$^+$: 404.07.

Example 10A rac-Methoxy-acetic acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 10 replacing the compound of example 1.

LC-MS (A): $t_R$=0.78 min; [M+H]$^+$: 476.49.

Example 10B rac-Isobutyric acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 10 replacing the compound of example 1 and isobutyrylchloride replacing methoxyacetyl chloride.

LC-MS (A): $t_R$=0.84 min; [M+H]$^+$: 474.12.

Example 11

(1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-ol or (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-ol Prepared according to procedures analogous to that of example 1, steps 1.9 and 1.10, using enantiomer A of rac-(1R*,8R*,12R*)-12-(2-hydroxy-ethyl)-tricyclo[6.3.2.0$^{2,7}$]trideca-2,4,6-trien-12-ol (intermediate 10.3) in step 1.9.

LC-MS (A): $t_R$=0.74 min; [M+H]$^+$: 404.08.

Example 11A

Isobutyric acid (1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-yl ester or isobutyric acid (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 11 replacing the compound of example 1 and isobutyrylchloride replacing methoxyacetyl chloride.

LC-MS (A): $t_R$=0.84 min; [M+H]$^+$:474.29.

Example 12

(1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-ol or (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-ol Prepared according to procedures analogous to that of example 1, steps 1.9 and 1.10, using enantiomer B of rac-(1R*,8R*,12R*)-12-(2-hydroxy-ethyl)-tricyclo[6.3.2.0$^{2,7}$]trideca-2,4,6-trien-12-ol (intermediate 10.3) in step 1.9.

LC-MS (A): $t_R$=0.74 min; [M+H]$^+$: 404.03

Example 12A

Isobutyric acid (1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-yl ester or isobutyric acid (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 12 replacing the compound of example 1 and isobutyrylchloride replacing methoxyacetyl chloride.

LC-MS (A): $t_R$=0.84 min; [M+H]$^+$: 474.30.

Example 13

(1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol or (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-ol 13.1 [3-(2-Amino-3-methoxy-phenylcarbamoyl)-propyl]-methyl-carbamic acid benzyl ester To a solution of 1.40 g 4-(benzyloxycarbonyl-methyl-amino)-butyric acid (obtained from 4-(methylamino)butyric acid and benzylchloroformate) in 25 mL THF were added 2.9 mL of DIPEA, 0.97 g of HOBt and 1.38 g EDC. After stirring for 5 min 0.80 g of 3-methoxy-benzene-1,2-diamine were added and the mixture was stirred for 3 h at rt. Sat. aq. NaHCO$_3$ solution was added, the phases were separated and the organic phase was washed with brine. The combined organic phases were dried over MgSO$_4$, and concentrated in vacuo.

LC-MS (A): $t_R$=0.80 min; [M+H]$^+$: 372.27.

13.2 [3-(4-Methoxy-1H-benzoimidazol-2-yl)-propyl]-methyl-carbamic acid benzyl ester To a mixture of crude [3-(2-amino-3-methoxy-phenylcarbamoyl)-propyl]methyl-carbamic acid benzyl ester acid in 7 mL toluene were added a few drops of DMF and 523 mg of TsOH and the reaction mixture was heated at 150° C. for 2.5 h in the microwave. Sat. aq. NaHCO$_3$ solution was added, the phases were separated and the organic phase was washed with brine. The combined organic phases were dried over MgSO$_4$, and concentrated in vacuo. Purification by CC EtOAc/MeOH (10:1) yielded 0.74 g of the desired compound as brown foam.

LC-MS (A): $t_R$=0.77 min; [M+H]$^+$: 354.40.

13.3 [3-(4-Methoxy-1H-benzoimidazol-2-yl)-propyl]-methyl-amine

A solution of 0.74 g of [3-(4-methoxy-1H-benzoimidazol-2-yl)-propyl]-methyl-carbamic acid benzyl ester in 20 mL EtOH was evacuated 3 times with $N_2$ before 90 mg of 10 wt % Pd/C were added. The reaction mixture was then stirred under a $H_2$ atmosphere (balloon) at rt overnight. Filtration over a pad of celite and washing with 100 mL EtOH yielded after concentration in vacuo 450 mg of the desired compound as beige solid.

LC-MS (A): $t_R$=0.45 min; [M+H]$^+$: 220.32.

13.4 (1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol or (1R, 8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-ol Prepared according to procedures analogous to that of example 1, steps 1.9 and 1.10, using enantiomer A of rac-(1R*,8R*,12R*)-12-(2-hydroxy-ethyl)-tricyclo[6.3.2.0$^{2,7}$]trideca-2,4,6-trien-12-ol (intermediate 10.3) in step 1.9 and [3-(4-methoxy-1H-benzoimidazol-2-yl)-propyl]-methyl-amine (intermediate 13.3) replacing [3-(1H-benzoimidazol-2-yl)-propyl]-methyl-amine in step 1.10.

LC-MS (A): $t_R$=0.71 min; [M+H]$^+$: 434.34.

Example 13A

Isobutyric acid (1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-yl ester or isobutyric acid (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 13 replacing the compound of example 1 and isobutyrylchloride replacing methoxyacetyl chloride.

LC-MS (A): $t_R$=0.80 min; [M+H]$^+$: 504.39.

Example 13B 3,3,3-Trifluoro-propionic acid (1S,8S,12S)-12-(2-{[3-(4-methoxy-1H-benzoimidazol-2-yl)-propyl]-methyl-amino}-ethyl)-tricyclo[6.3.2.02,7]trideca-2,4,6-trien-12-yl ester or 3,3,3-trifluoro-propionic acid (1R,8R,12R)-12-(2-{[3-(4-methoxy-1H-benzoimidazol-2-yl)-propyl]-methyl-amino}-ethyl)-tricyclo[6.3.2.02,7]trideca-2,4,6-trien-12-yl ester This compound was prepared using a method analogous to that of example 1A, step 1.A1, the compound of example 13 replacing the compound of example 1 and 3,3,3-trifluoro-proprionyl chloride replacing methoxyacetyl chloride.

LC-MS (A): $t_R$=0.82 min; [M+H]$^+$: 544.44.

Example 14

(1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol or (1R, 8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12 -ol

14.1 3-Methoxy-6-methyl-benzene-1,2-diamine

3-Methoxy-6-methyl-benzene-1,2-diamine was synthesized by suspending 3.3 g of 1-methoxy-4-methyl-2,3-dinitro-benzene (Can. J. Chem. 65, 1233-1240, 1987) in 100 mL EtOH, evacuating 3 times with $N_2$ and addition of 450 mg of 10wt % Pd/C. The reaction mixture was stirred under a $H_2$ atmosphere (balloon) overnight. Filtration over a pad of celite and washing with 100 mL EtOH yielded after concentration in vacuo 2.2 g of the desired compound as brown oil.

LC-MS (A): $t_R$=0.45 min; [M+H]$^+$: 153.35.

14.2 [3-(4-Methoxy-7-methyl-1H-benzoimidazol-2-yl)-propyl]-methyl-amine

Prepared according to procedures analogous to that of example 13, steps 13.1 to 13.3, intermediate 14.1 replacing 3-methoxy-benzene-1,2-diamine in step 13.1.

LC-MS (A): $t_R$=0.52 min; [M+H]$^+$: 234.18.

14.3 (1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol or (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-ol Prepared according to procedures analogous to that of example 1, steps 1.9 and 1.10, using enantiomer A of rac-(1R*,8R*,12R*)-12-(2-hydroxy-ethyl)-tricyclo[6.3.2.0$^{2,7}$]trideca-2,4,6-trien-12-ol (intermediate 10.3) in step 1.9 and [3-(4-methoxy-7-methyl-1H-benzoimidazol-2-yl)-propyl]-methyl-amine (intermediate 14.2) replacing [3-(1H-benzoimidazol-2-yl)-propyl]-methyl-amine in step 1.10.

LC-MS (A): $t_R$=0.73 min; [M+H]$^+$: 448.38.

Example 14A

Isobutyric acid (1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-yl ester or isobutyric acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester This compound was prepared using a method analogous to that of example 1A, step 1.A1, the compound of example 14 replacing the compound of example 1 and isobutyrylchloride replacing methoxyacetyl chloride.

LC-MS (A): $t_R$=0.84 min; [M+H]$^+$: 518.24.

Example 14B 3,3,3-Trifluoro-propionic acid (1S,8S,12S)-12-(2-{[3-(4-methoxy-7-methyl-1H-benzoimidazol-2-yl)-propyl]-methyl-amino}-ethyl)-tricyclo[6.3.2.0$^{2,7}$]tridec-2,4,6-trien-12-yl ester or 3,3,3-trifluoro-propionic acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]tridec-2,4,6-trien-12-yl ester This compound was prepared using a method analogous to that of example 1A, step 1.A1, the compound of example 14 replacing the compound of example 1 and 3,3,3-trifluoro-proprionyl chloride replacing methoxyacetyl chloride.
LC-MS (A): $t_R$=0.83 min; [M+H]$^+$: 558.28.

Example 15 rac-(1R*,8R*,12R*)-12-(2-{[3-(4,7-Dimethoxy-1H-benzoimidazol-2-yl)-propyl]-methyl-amino}-ethyl)-tricyclo[6.3.2.0$^{2,7}$]tridec-2,4,6-trien-12-ol

15.1 3,6-Dimethoxy-benzene-1,2-diamine 3,6-Dimethoxy-benzene-1,2-diamine was synthesized by dissolving 6.0 g of 1,4-dimethoxy-2,3-dinitro-benzene (Eur. J. Org. Chem. 2006, 2786-2794) in 220 mL EtOH, evacuating 3 times with $N_2$ and adding 600 mg of 10wt % Pd/C. The reaction was stirred under a $H_2$ atmosphere (balloon). Another 300 mg of 10wt % Pd/C were added after 2 days and the mixture was stirred for another 24 h. Filtration over a pad of celite and washing with EtOH and EtOAc yielded after concentration in vacuo 4.3 g of the desired compound as black solid.
LC-MS (A): $t_R$=0.48 min; [M+H]$^+$: 169.09.

15.2 [3-(4,7-Dimethoxy-1H-benzoimidazol-2-yl)-propyl]-methyl-amine

Prepared according to procedures analogous to that of example 13, steps 13.1 to 13.3, intermediate 15.1 replacing 3-methoxy-benzene-1,2-diamine in step 13.1.
LC-MS (A): $t_R$=0.57 min; [M+H]$^+$: 250.13.

15.3 rac-(1R*,8R*,12R*)-12-(2-{[3-(4,7-Dimethoxy-1H-benzoimidazol-2-yl)-propyl]-methyl-amino}-ethyl)-tricyclo[6.3.2.0$^{2,7}$]tridec-2,4,6-trien-12-ol Prepared according to procedures analogous to that of example 1, steps 1.9 and 1.10, rac-(1R*,8R*,12R*)-12-(2-hydroxy-ethyl)-tricyclo[6.3.2.0$^{2,7}$]tridec-2,4,6-trien-12-ol (step 10.2) replacing rac-(1R*,8R*,9R*)-9-(2-hydroxy-ethyl)-tricyclo[6.2.2.0$^{2,7}$]dodeca-2,4,6-trien-9-ol in step 1.9 and [3-(4,7-dimethoxy-1H-benzoimidazol-2-yl)-propyl]-methyl-amine (intermediate 15.2) replacing [3-(1H-benzoimidazol-2-yl)-propyl]-methyl-amine in step 1.10.
LC-MS (A): $t_R$=0.78 min; [M+H]$^+$: 464.17.

Example 15A rac-Isobutyric acid (1R*,8R*,12R*)-12-(2-{[3-(4,7-dimethoxy-1H-benzoimidazol-2-yl)-propyl]-methyl-amino}-ethyl)-tricyclo[6.3.2.0$^{2,7}$]tridec-2,4,6-trien-12-yl ester This compound was prepared using a method analogous to that of example 1A, step 1.A1, the compound of example 15 replacing the compound of example 1 and isobutyrylchloride replacing methoxyacetyl chloride.
LC-MS (A): $t_R$=0.88 min; [M+H]$^+$: 534.35.

Example 16

(1S,8S,12S)-12-(2-{[3-(4,7-Dimethoxy-1H-benzoimidazol-2-yl)-propyl]-methyl-amino}-ethyl)-tricyclo[6.3.2.0$^{2,7}$]tridec-2,4,6-trien-12-ol or (1R,8R,12R)-12-(2-{[3-(4,7-dimethoxy-1H-benzoimidazol-2-yl)-propyl]-methyl-amino}-ethyl)-tricyclo[6.3.2.0$^{2,7}$]tridec-2,4,6-trien-12-ol Prepared according to procedures analogous to that of example 1, steps 1.9 and 1.10, using enantiomer A of rac-(1R*,8R*,12R*)-12-(2-hydroxy-ethyl)-tricyclo[6.3.2.0$^{2,7}$]tridec-2,4,6-trien-12-ol (intermediate 10.3) in step 1.9 and [3-(4,7-dimethoxy-1H-benzoimidazol-2-yl)-propyl]-methyl-amine (intermediate 15.2) replacing [3-(1H-benzoimidazol-2-yl)-propyl]-methyl-amine in step 1.10.
LC-MS (A): $t_R$=0.78 min; [M+H]$^+$: 464.29.

Example 16A

Isobutyric acid (1S,8S,12S)-12-(2-{[3-(4,7-dimethoxy-1H-benzoimidazol-2-yl)-propyl]-methyl-amino}-ethyl)-tricyclo[6.3.2.0$^{2,7}$]tridec-2,4,6-trien-12-yl ester or isobutyric acid (1R,8R,12R)-12-(2-{[3-(4,7-dimethoxy-1H-benzoimidazol-2-yl)-propyl]-methyl-amino}-ethyl)-tricyclo[6.3.2.0$^{2,7}$]tridec-2,4,6-trien-12-yl ester This compound was prepared using a method analogous to that of example 1A, step 1.A1, the compound of example 16 replacing the compound of example 1 and isobutyrylchloride replacing methoxyacetyl chloride.
LC-MS (A): $t_R$=0.87 min; [M+H]$^+$: 534.56.

Biological Tests
In Vitro Assay L Channel

The L channel antagonistic activity ($IC_{50}$ values) of the compounds of formula (I) is determined in accordance with the following experimental method.

Human embryonic kidney (HEK293) cells expressing the human $Ca_v1.2$ channel in addition to the auxiliary subunits β-2a and α2δ-1, are grown in culture medium (DMEM containing 10% heat-inactivated fetal calf serum (FCS), 100 U/ml penicillin, 100 μg/ml streptomycin, 100 μg/ml G418, 40μg/ml zeocin and 100 μg/ml hygromycin). The cells are seeded at 20.000 cells/well into 384-well black clear bottom sterile plates (poly-L-lysine-coated, Becton Dickinson). The seeded plates are incubated overnight at 37° C. in 5% $CO_2$. The KCl solution is prepared as 80 mM stock solution in assay buffer (HBSS containing 0.1% BSA, 20 mM HEPES, 0.375 g/l NaHCO$_3$, adjusted to pH 7.4 with NaOH) for use in the assay at a final concentration of 20 mM. Antagonists are prepared as 10 mM stock solutions in DMSO, then diluted in 384 w plates first in DMSO, then in assay buffer to obtain 3× stocks. On the day of the assay, 25 μl of staining buffer (HBSS containing 20 mM HEPES, 0.375 g/l NaHCO$_3$, and 3 μM of the fluorescent calcium indicator fluo-4 AM (1 mM stock solution in DMSO, containing 10% pluronic) is added to each well of the seeded plate. The 384-well cell-plates are incubated for 60 min at 37° C. in 5% $CO_2$ followed by washing with 2×50 μl per well using assay buffer leaving 50 μl/well of this buffer for equilibration at room temperature (30-60 min). Within the Fluorescent Imaging Plate Reader (FLIPR, Molecular Devices), antagonists are added to the plate in a volume of 25 μl/well, incubated for 3 min and finally 25 μl/well of KCl solution is added for cellular depolarization.

Fluorescence is measured for each well at 2 second intervals for 8 minutes, and the area under the curve of each fluorescence peak is compared to the area of the fluorescence peak induced by 20 mM KCl with vehicle in place of antagonist. For each antagonist, the $IC_{50}$ value (the concentration (in nM) of compound needed to inhibit 50% of the KCl-induced fluorescence response) up to 10 µM is determined.

Compounds of examples 13, 13A, 13B, 14, 14A, 14B, 15, 15A, 16 and 16A have not been tested in this assay. $IC_{50}$ values of the remaining 25 example compounds are in the range of 1022 to 8739 nM with an average of 2536 nM.

In Vitro Assay T Channel:

The T channel antagonistic activity ($IC_{50}$ values) of the compounds of formula (I) is determined in accordance with the following experimental method and data for example compounds are shown in Table 1.

Human embryonic kidney (HEK293) cells expressing the human $Ca_v3.1$ $Ca_v3.2$ or $Ca_v3.3$ channel, respectively, are grown in culture medium (DMEM containing 10% heat-inactivated fetal calf serum (FCS), 100 U/ml penicillin, 100 µg/ml streptomycin and 1 mg/ml G418). The cells are seeded at 20.000 cells/well into 384-well black clear bottom sterile plates (poly-L-lysine-coated, Becton Dickinson). The seeded plates are incubated overnight at 37° C. in 5% $CO_2$. The $Ca^{2+}$ solution is prepared as 100 mM stock solution in 100 mM tetraethylammoniumchloride (TEA-chloride), 50 mM HEPES, 2.5 mM $CaCl_2$, 5 mM KCl, 1 mM $MgCl_2$, adjusted to pH 7.2 with TEA-hydroxide, for use in the assay at a final concentration of 10 mM. Antagonists are prepared as 10 mM stock solutions in DMSO, then diluted in 384 w plates first in DMSO, then in 100 mM TEA-chloride, 50 mM HEPES, 2.5 mM $CaCl_2$, 5 mM KCl, 1 mM $MgCl_2$, adjusted to pH 7.2 with TEA-hydroxide, to obtain 9× stocks. On the day of the assay, 25 µl of staining buffer (HBSS containing 20 mM HEPES, 0.375 g/l $NaHCO_3$ and 3 µM of the fluorescent calcium indicator fluo-4 AM (1 mM stock solution in DMSO, containing 10% pluronic) is added to each well of the seeded plate. The 384-well cell-plates are incubated for 60 min at 37° C. in 5% $CO_2$ followed by washing with 2×50 µl per well using HBSS containing 0.1% BSA, 20 mM HEPES, 0.375 g/l $NaHCO_3$, leaving 50 µl/well of this buffer for equilibration at room temperature (30-60 min). Within the Fluorescent Imaging Plate Reader (FLIPR, Molecular Devices), antagonists are added to the plate in a volume of 6.25 µl/well, incubated for 3 min, and finally 6.25 µl/well of $Ca^{2+}$ solution is added. Fluorescence is measured for each well at 2 second intervals for 8 minutes, and the area under the curve of each fluorescence peak is compared to the area of the fluorescence peak induced by 10 mM $Ca^{2+}$ with vehicle in place of antagonist. For each antagonist, the $IC_{50}$ value (the concentration (in nM) of compound needed to inhibit 50% of the $Ca^{2+}$-induced fluorescence response) up to 10 µM is determined.

Effect on Isolated Hearts According to the Langendorff Method (Lgdff)

The compounds were tested for their potential to reduce blood pressure and their effect on the contractility of the heart muscle. $EC_{50}$ values on isolated mouse hearts were determined according to Literature (Doring H J., The isolated perfused heart according to Langendorff technique—function—application, Physiol. Bohemoslov. 1990, 39(6), 481-504; Kligfield P, Homer H, Brachfeld N., A model of graded ischemia in the isolated perfused rat heart, J. Appl. Physiol. 1976 June, 40(6), 1004-8).

15 example compounds have been measured using the procedure described above for the Langendorff experiment. Results for selected compounds are given in table 2.

TABLE 2

| Compound of Example | Lgdff $EC_{50}$ [nM] |
|---|---|
| 1B | 42 |
| 9A | 30 |
| 11A | 22 |
| 13B | 6 |

The invention claimed is:
1. A compound of the formula (I)

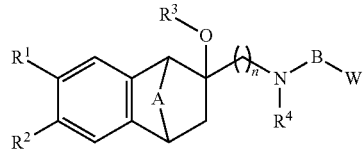

Formula (I)

wherein
$R^1$ and $R^2$ independently represent hydrogen or halogen;
A represents a linear $(C_{1-3})$alkan-diyl chain, wherein said linear $(C_{1-3})$alkan-diyl chain is optionally substituted with one or more methyl;
$R^3$ represents hydrogen, $(C_{1-5})$alkyl, or $—CO—R^{31}$;
$R^{31}$ represents $(C_{1-5})$alkyl, $(C_{1-3})$fluoroalkyl, $(C_{3-6})$cycloalkyl, $(C_{3-6})$cycloallcyl-$(C_{1-3})$alkyl, $(C_{1-5})$alkoxy, $(C_{1-2})$alkoxy-$(C_{1-3})$alkyl, or $R^{32}R^{33}N—$;
$R^{32}$ represents $(C_{1-5})$alkyl;
$R^{33}$ represents hydrogen, or $(C_{1-5})$alkyl;
n represents the integer 1, 2, 3, or 4;
B represents a group $—(CH_2)_m—$, wherein m represents the integer 1, 2, 3, 4, or 5; or B together with $R^4$ and the nitrogen atom to which B and $R^4$ are attached forms a 4-

TABLE 1

| Compound of example | $IC_{50}$ [nM] | Compound of example | $IC_{50}$ [nM] | Compound of example | $IC_{50}$ [nM] | Compound of example | $IC_{50}$ [nM] |
|---|---|---|---|---|---|---|---|
| 1 | 2846 | 1A | 1527 | 1B | 2074 | 1C | 969 |
| 2 | 2900 | 2A | 1789 | 3 | 2248 | 4 | 1216 |
| 5 | >10000 | 5A | 5178 | 6 | 1355 | 6A | 751 |
| 7 | 2260 | 7A | 1112 | 8 | 953 | 8A | 6100 |
| 9 | 1854 | 9A | 1400 | 10 | 1578 | 10A | 814 |
| 10B | 1307 | 11 | 521 | 11A | 1046 | 12 | 631 |
| 12A | 783 | 13 | 1221 | 13A | 544 | 13B | 653 |
| 14 | 736 | 14A | 191 | 14B | 514 | 15 | NA |
| 15A | NA | 16 | NA | 16A | NA | | |

NA = not available/not tested to 6-membered saturated ring, wherein said ring may optionally be mono-substituted with phenyl;

$R^4$ represents hydrogen; $(C_{1-5})$alkyl; $(C_{1-2})$alkoxy-$(C_{1-3})$alkyl; $(C_{1-3})$fluoroalkyl; $(C_{3-6})$cycloalkyl; or $(C_{3-6})$cycloalkyl-$(C_{1-3})$alkyl; or $R^4$ together with B and the nitrogen atom to which $R^4$ and B are attached forms a 4- to 6-membered saturated ring, wherein said ring may optionally be mono-substituted with phenyl; and W represents

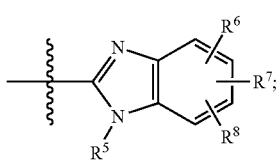

wherein $R^5$ represents hydrogen, or $(C_{1-5})$alkyl; and $R^6$, $R^7$ and $R^8$ independently represent hydrogen, halogen, $(C_{1-5})$alkyl, hydroxy, $(C_{1-5})$alkoxy, —O—CO—$(C_{1-5})$alkyl, $(C_{1-3})$fluoroalkyl, $(C_{1-3})$fluoroalkoxy, —COOH, —CO—$(C_{1-5})$alkoxy, $(C_{1-2})$alkoxy-$(C_{1-4})$alkoxy, or —NH—CO—$(C_{1-5})$alkyl, in a free or a pharmaceutically acceptable salt form of such a compound.

2. The compound of formula (I) according to claim 1, the configuration of the bridged tetrahydronaphthalene moiety is such that the $R^3$—O— substituent and the bridge A of the tetrahydronaphthalene moiety are in cis relation, in a free or a pharmaceutically acceptable salt form of such a compound.

3. The compound of formula (I) according to claim 1, wherein $R^1$ and $R^2$ both represent hydrogen, in a free or a pharmaceutically acceptable salt form of such a compound.

4. The compound of formula (I) according to claim 1, wherein A represents —$(CH_2)_p$—, wherein p represents the integer 2 or 3, in a free or a pharmaceutically acceptable salt form of such a compound.

5. The compound of formula (I) according to claim 1, wherein $R^3$ represents hydrogen, or —CO—$R^{31}$, in a free or a pharmaceutically acceptable salt form of such a compound.

6. The compounds of formula (I) according to claim 1, wherein $R^{31}$ represents $(C_{1-5})$alkyl, $(C_{1-3})$fluoroalkyl, $(C_{3-6})$cycloalkyl, or $(C_{1-2})$alkoxy-$(C_{1-3})$alkyl, in a free or a pharmaceutically acceptable salt form of such a compound.

7. The compounds of formula (I) according to claim 1, wherein B represents a group —$(CH_2)_m$—, wherein m represents the integer 3, in a free or a pharmaceutically acceptable salt form of such a compound.

8. The compounds of formula (I) according to claim 1, wherein n represents the integer 2, in a free or a pharmaceutically acceptable salt form of such a compound.

9. The compound of formula (I) according to claim 1, wherein $R^4$ represents $(C_{1-5})$alkyl, in a free or a pharmaceutically acceptable salt form of such a compound.

10. The compound of formula (I) according to claim 9, wherein $R^6$, $R^7$ and $R^8$ independently represent hydrogen, halogen, $(C_{1-5})$alkyl, $(C_{1-5})$alkoxy, $(C_{1-3})$fluoroalkyl, or $(C_{1-3})$fluoroalkoxy, in a free or a pharmaceutically acceptable salt form of such a compound.

11. The compound of formula (I) according to claim 1, wherein $R^5$ represents hydrogen, in a free or a pharmaceutically acceptable salt form of such a compound.

12. The compound of formula (I) according to claim 1, selected from the following compounds:

(1R*,8R*,9R*)-9-(2-{[3-(1H-Benzoimidazol-2-yl)-propyl]-methyl-amino}-ethyl)-tricyclo[6.2.2.0$^{2,7}$]dodeca-2,4,6-trien-9-ol;

Methoxy-acetic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Isobutyric acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Cyclopropanecarboxylic acid (1R*,8R*,9R*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

(1S,8S,9S)-9-(2-{[3-(1H-Benzoimidazol-2-yl)-propyl]-methyl-amino}-ethyl)-tricyclo[6.2.2.0$^{2,7}$]dodeca-2,4,6-trien-9-ol;

(1R,8R,9R)-9-(2-{[3-(1H-Benzoimidazol-2-yl)-propyl]methyl-amino }-ethyl)-tricyclo[6.2.2.0$^{2,7}$]dodeca-2,4,6-trien-9-ol;

Isobutyric acid (1S,8S,9S)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

Isobutyric acid (1R,8R,9R)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

(1R*,8R*,9R*)-[3-(1H-Benzoimidazol-2-yl)-propyl]2-(9-methoxy-tricyclo[6.2.2.0$^{2,7}$]dodeca-2,4,6-trien-9-yl)-ethyl]-methyl-amine;

(1R*,8R*,9S*)-9-(2-{[3 -(1H-Benzoimidazol-2-yl)-propyl]-methyl-amino}-ethyl-tricyclo[6.2.2.0$^{2,7}$]dodeca-2,4,6-trien-9-ol;

Isobutyric acid (1R*,8R*,9S*)-9-(2-{[3-(1H-benzoimidazol-2-yl)-propyl]-methyl-amino}-ethyl)-tricyclo[6.2.2.0$^{2,7}$]dodeca-2,4,6-trien-9-yl ester;

(1R*,8R*,9R*)-9-{2-[4-(1H-Benzoimidazol-2-yl)-piperidin-1-yl]-ethyl}-tricyclo[6.2.2.0$^{2,7}$]dodeca-2,4,6-trien-9-ol;

Isobutyric acid (1R*,8R*,9R*)-9-{2-[4-(1H-benzoimidazol-2-yl)-piperidin-1-yl]-ethyl }-tricyclo[6.2.2.0$^{2,7}$]dodeca-2,4,6-trien-9-yl ester;

(1R*,8R*,9R*)-9-{2-[(3RS)-3-(1H-Benzoimidazol-2-yl)-piperidin-1-yl]ethyl}-tricyclo[6.2.2.0$^{2,7}$]dodeca-2,4,6-trien-9-ol;

Isobutyric acid (1R*,8R*,9R*)-9-{2-[(3RS)-3-(1H-benzoimidazol-2-yl)-piperidin-1 -yl]-ethyl }-tricyclo[6.2.2.0$^{2,7}$]dodeca-2,4,6-trien-9-yl ester;

(1R*,8R*,9R*)-9-{2-[4-(1H-Benzoimidazol-2-yl)-4-phenyl-piperidin-1 -yl]-ethyl}-tricyclo[6.2.2.0$^{2,7}$]dodeca-2,4,6-trien-9-ol;

Isobutyric acid (1R*,8R*,9R*)-9-{2-[4-(1H-benzoimidazol-2-yl)-4-phenyl-piperidin-1-yl]-ethyl)}-tricyclo[6.2.2.0$^{2,7}$]dodeca-2,4,6-trien-9-yl ester;

(1R*,8R*,9R*)-9-(2-{[3-(1H-Benzoimidazol-2-yl)-propyl]-methyl-amino}-ethyl)-4,5-difluoro-tricyclo[6.2.2.0$^{2,7}$]dodeca-2,4,6-trien-9-ol;

Isobutyric acid (1R*,8R*,9R*)-9-(2-{[3-(1H-benzoimidazol-2-yl)-propyl]-methyl-amino}-ethyl)-4,5-difluoro-tricyclo[6.2.2.0$^{2,7}$]dodeca-2,4,6-trien-9-yl ester;

(1R*,8R*,12R*)-12-(2-{[3-(1H-Benzoimidazol-2-yl)-propyl]methyl-amino}-ethyl)-tricyclo[6.3.2.0$^{2,7}$]trideca-2,4,6-trien-12-ol;

Methoxy-acetic acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;

Isobutyric acid (1R*,8R*,12R*)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;

(1S,8S ,12S)-12-(2-{[3-(1H-Benzoimidazol-2-yl)-propyl]-methyl-amino }-ethyl)-tricyclo[6.3.2.0$^{2,7}$]trideca-2,4,6-trien-12-ol;

(1R,8R,12R)-12-(2-{[3-(1H-Benzoimidazol-2-yl)-propyl]-methyl-amino}-ethyl)-tricyclo[6.3.2.0$^{2,7}$]trideca-2,4,6-trien-12-ol;

Isobutyric acid (1S,8S,12S)-12-(2-{[3-(1H-Benzoimidazol-2-yl)-propyl]-methyl-amino}-ethyl)-tricyclo[6.3.2.0$^{2,7}$]trideca-2,4,6-trien-12-yl ester;
Isobutyric acid (1R,8R,12R)-12-(2-{[3-(1H-benzoimidazol-2-yl)-propyl]-methyl-amino}-ethyl)-tricyclo[6.3.2.0$^{2,7}$]trideca-2,4,6-trien-12-yl ester;
(1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol;
(1R,8R,12R)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-ol;
Isobutyric acid (1S,8S,12S)-12-(2-{[3-(4-Methoxy-1H-benzoimidazol-2-yl)-propyl]-methyl-amino}-ethyl)-tricyclo[6.3.2.0$^{2,7}$]trideca-2,4,6-trien-12-yl ester;
Isobutyric acid (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester;
3,3,3-Trifluoro-propionic acid (1S,8S,12S)-12-(2-{[3-(4-methoxy-1H-benzoimidazol-2-yl)-propyl]methyl-amino}-ethyl)-tricyclo[6.3.2.0$^{2,7}$]trideca-2,4,6-trien-12-yl ester;
3,3,3-Trifluoro-propionic acid (1R,8R,12R)-12-(2-{[3-(4-methoxy-1H-benzoimidazol-2-yl)-propyl]-methyl-amino}-ethyl)-tricyclo[6.3.2.0$^{2,7}$]trideca-2,4,6-trien-12-yl ester;
(1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol;
(1R,8R,12R)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-ol;
Isobutyric acid (1S,8S,12S)-12-(2-{[3-(4-Methoxy-7-methyl-1H-benzoimidazol-2-yl)-propyl]-methyl-amino}-ethyl)-tricyclo[6.3.2.0$^{2,7}$]trideca-2,4,6-trien-12-yl ester;
Isobutyric acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;
3,3,3-Trifluoro-propionic acid (1S,8S,12S)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;
3,3,3-Trifluoro-propionic acid (1R,8R,12R)-12-(2-{[3-(4-methoxy-7-methyl-1H-benzoimidazol-2-yl)-propyl]-methyl-amino}-ethyl)-tricyclo[6.3.2.0$^{2,7}$]trideca-2,4,6-trien-12-yl ester;
(1R*,8R*,12R*)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol;
Isobutyric acid (1R*,8R*,12R*)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester;
(1S,8S,12S)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol;
(1R,8R,12R)-12-(2-{[3-(4,7-Dimethoxy-1H-benzoimidazol-2-yl)-propyl]-methyl-amino}-ethyl)-tricyclo[6.3.2.0$^{2,7}$]trideca-2,4,6-trien-12-ol ;
Isobutyric acid (1S,8S,12S)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester; and
Isobutyric acid (1R,8R,12R)-12-(2-{[3-(4,7-dimethoxy-1H-benzoimidazol-2-yl)-propyl]-methyl-amino}-ethyl)-tricyclo[6.3.2.0$^{2,7}$]trideca-2,4,6-trien-12-yl ester, in a free or a pharmaceutically acceptable salt form of such a compound.

13. A pharmaceutical composition containing, as active principle, a compound of formula (I) according to claim 1, in a free or a pharmaceutically acceptable salt form, and at least one therapeutically inert excipient.

14. A method of treatment of a disease or disorder associated with cardiovascular disorders, wherein said method comprises administering to a subject in need thereof an effective amount of a compound of formula (I) according to claim 1 or a pharmaceutical composition according to claim 13, wherein said disease or disorder is selected from the group consisting of: chronic stable angina, hypertension, ischemia, renal ischemia, cardiac ischemia, cardiac arrhythmias, artrial fibrillation, cardiac hypertrophy, and congestive heart failure.

* * * * *